(12) United States Patent
Altarac et al.

(10) Patent No.: US 10,058,358 B2
(45) Date of Patent: *Aug. 28, 2018

(54) SYSTEMS AND METHODS FOR POSTERIOR DYNAMIC STABILIZATION OF THE SPINE

(71) Applicant: The Board of Trustees of the Leland Stanford Junior University, Palo Alto, CA (US)

(72) Inventors: Moti Altarac, Irvine, CA (US); J. Christopher Flaherty, Topsfield, MA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/268,844

(22) Filed: Sep. 19, 2016

(65) Prior Publication Data

US 2017/0156763 A1  Jun. 8, 2017

Related U.S. Application Data

(63) Continuation of application No. 14/154,094, filed on Jan. 13, 2014, now Pat. No. 9,445,843, which is a
(Continued)

(51) Int. Cl.
*A61B 17/70* (2006.01)
*A61B 17/00* (2006.01)

(52) U.S. Cl.
CPC .... *A61B 17/7065* (2013.01); *A61B 2017/00557* (2013.01)

(58) Field of Classification Search
CPC .......... A61F 2/44; A61F 2/441; A61F 2/4611; A61F 2/46; A61F 2/4405; A61F 2/30732;
(Continued)

(56) References Cited

U.S. PATENT DOCUMENTS 2,248,054 A   7/1941 Becker
2,677,369 A   5/1954 Knowles
(Continued)

FOREIGN PATENT DOCUMENTS

CA    268461 A   2/1927
CN    2794456 Y   7/2006
(Continued)

OTHER PUBLICATIONS

ASNR Neuroradiology Patient Information website, Brain and Spine Imaging: A Patient's Guide to Neuroradiology; Myelography; http://www.asnr.org/patientinfo/procedures/myelography.shtml#sthash.sXIDOxWq.dpbs, Copyright 2012-2013.
(Continued)

*Primary Examiner* — Pedro Philogene
(74) *Attorney, Agent, or Firm* — Perkins Coie LLP

(57) ABSTRACT

Devices, systems and methods for dynamically stabilizing the spine are provided. The devices include an expandable spacer having an undeployed configuration and a deployed configuration, wherein the spacer has axial and radial dimensions for positioning between the spinous processes of adjacent vertebrae. The systems include one or more spacers and a mechanical actuation means for delivering and deploying the spacer. The methods involve the implantation of one or more spacers within the interspinous space.

24 Claims, 14 Drawing Sheets

Related U.S. Application Data continuation of application No. 12/844,365, filed on Jul. 27, 2010, now Pat. No. 8,628,574, which is a continuation of application No. 11/305,820, filed on Dec. 15, 2005, now Pat. No. 7,763,074, which is a continuation-in-part of application No. 11/190,496, filed on Jul. 26, 2005, now Pat. No. 8,409,282, which is a continuation-in-part of application No. 11/079,006, filed on Mar. 10, 2005, now Pat. No. 8,012,207, which is a continuation-in-part of application No. 11/052,002, filed on Feb. 4, 2005, now Pat. No. 8,317,864, which is a continuation-in-part of application No. 11/006,502, filed on Dec. 6, 2004, now Pat. No. 8,123,807, which is a continuation-in-part of application No. 10/970,843, filed on Oct. 20, 2004, now Pat. No. 8,167,944.

(58) Field of Classification Search
CPC ..... A61B 17/88; A61B 17/7065; A61B 17/70; A61B 17/7062; A61B 17/7061; A61B 17/7067; A61B 17/7068; A61B 17/7064; A61B 17/8841; A61B 17/8802; A61B 17/7097
USPC .............. 623/17.11–17.16; 606/90, 246–279
See application file for complete search history.

(56) References Cited

U.S. PATENT DOCUMENTS

| | | |
|---|---|---|
| 3,242,120 A | 3/1966 | Steuber |
| 3,486,505 A | 12/1969 | Morrison |
| 3,648,691 A | 3/1972 | Lumb et al. |
| 3,986,383 A * | 10/1976 | Petteys .................... B21D 1/08 269/48.1 |
| 4,545,374 A | 10/1985 | Jacobson |
| 4,632,101 A | 12/1986 | Freedland |
| 4,685,447 A | 8/1987 | Iversen et al. |
| 4,799,484 A | 1/1989 | Smith et al. |
| 4,863,476 A | 9/1989 | Shepperd |
| 4,895,564 A | 1/1990 | Farrell |
| 4,986,831 A | 1/1991 | King et al. |
| 5,011,484 A | 4/1991 | Breard et al. |
| 5,015,247 A | 5/1991 | Michelson |
| 5,019,081 A | 5/1991 | Watanabe |
| 5,040,542 A | 8/1991 | Gray |
| 5,059,193 A * | 10/1991 | Kuslich ................. F16B 13/061 606/247 |
| 5,092,866 A | 3/1992 | Breard et al. |
| 5,178,628 A | 1/1993 | Otsuka et al. |
| 5,180,393 A | 1/1993 | Commarmond et al. |
| 5,182,281 A | 1/1993 | Frigola-Constansa et al. |
| 5,188,281 A | 2/1993 | Fujiwara et al. |
| 5,192,281 A | 3/1993 | de la Caffiniere |
| 5,195,526 A | 3/1993 | Michelson |
| 5,298,253 A | 3/1994 | LeFiles et al. |
| 5,368,594 A | 11/1994 | Martin et al. |
| 5,390,683 A | 2/1995 | Pisharodi |
| 5,415,661 A | 5/1995 | Holmes |
| 5,456,722 A | 10/1995 | McLeod et al. |
| 5,462,738 A | 10/1995 | LeFiles et al. |
| 5,472,452 A | 12/1995 | Trott |
| 5,484,437 A | 1/1996 | Michelson |
| 5,487,739 A | 1/1996 | Aebischer et al. |
| 5,489,308 A | 2/1996 | Kuslich et al. |
| 5,496,318 A | 3/1996 | Howland et al. |
| 5,531,748 A | 7/1996 | de la Caffiniere et al. |
| 5,549,679 A | 8/1996 | Kuslich |
| 5,571,189 A | 11/1996 | Kuslich |
| 5,591,165 A | 1/1997 | Jackson |
| 5,609,634 A | 3/1997 | Voydeville et al. |
| 5,609,636 A | 3/1997 | Kohrs et al. |
| 5,645,599 A | 7/1997 | Samani et al. |
| 5,654,599 A | 8/1997 | Casper |
| 5,658,337 A | 8/1997 | Kohrs et al. |
| 5,674,295 A | 10/1997 | Ray et al. |
| 5,700,264 A | 12/1997 | Zucherman et al. |
| 5,725,582 A | 3/1998 | Bevan et al. |
| 5,741,253 A | 4/1998 | Michelson |
| 5,746,720 A | 5/1998 | Stouder, Jr. |
| 5,762,629 A | 6/1998 | Kambin |
| 5,836,948 A | 11/1998 | Zucherman et al. |
| 5,860,977 A | 1/1999 | Zucherman et al. |
| 5,863,948 A | 1/1999 | Epstein et al. |
| 5,876,404 A | 3/1999 | Zucherman et al. |
| RE36,211 E | 5/1999 | Nonomura et al. |
| 5,904,636 A | 5/1999 | Chen et al. |
| 5,904,686 A | 5/1999 | Zucherman et al. |
| 5,928,207 A | 7/1999 | Pisano et al. |
| 5,948,017 A | 9/1999 | Taheri |
| 5,972,015 A | 10/1999 | Scribner et al. |
| 6,039,761 A | 3/2000 | Li et al. |
| 6,045,552 A | 4/2000 | Zucherman et al. |
| 6,048,342 A | 4/2000 | Zucherman et al. |
| 6,048,345 A | 4/2000 | Berke et al. |
| 6,066,154 A | 5/2000 | Reiley et al. |
| 6,068,630 A | 5/2000 | Zucherman et al. |
| 6,074,390 A | 6/2000 | Zucherman et al. |
| 6,080,155 A | 6/2000 | Michelson |
| 6,080,157 A | 6/2000 | Cathro et al. |
| 6,090,112 A | 7/2000 | Zucherman et al. |
| 6,096,038 A | 8/2000 | Michelson |
| 6,102,928 A | 8/2000 | Bonutti |
| D433,193 S | 10/2000 | Gaw et al. |
| 6,132,464 A | 10/2000 | Martin et al. |
| 6,149,642 A | 11/2000 | Gerhart et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,215 A | 12/2000 | Urbahns et al. |
| 6,179,873 B1 | 1/2001 | Zientek |
| 6,183,471 B1 | 2/2001 | Zucherman et al. |
| 6,190,387 B1 | 2/2001 | Zucherman et al. |
| 6,225,048 B1 | 5/2001 | Soderberg-Naucler et al. |
| 6,235,030 B1 | 5/2001 | Zucherman et al. |
| 6,238,397 B1 | 5/2001 | Zucherman et al. |
| 6,264,651 B1 | 7/2001 | Underwood et al. |
| 6,264,656 B1 | 7/2001 | Michelson |
| 6,267,765 B1 | 7/2001 | Taylor et al. |
| 6,270,498 B1 | 8/2001 | Michelson |
| 6,280,444 B1 | 8/2001 | Zucherman et al. |
| 6,312,431 B1 | 11/2001 | Asfora |
| 6,328,730 B1 | 12/2001 | Harkrider, Jr. |
| 6,332,882 B1 | 12/2001 | Zucherman et al. |
| 6,332,883 B1 | 12/2001 | Zucherman et al. |
| 6,336,930 B1 | 1/2002 | Stalcup et al. |
| 6,348,053 B1 | 2/2002 | Cachia |
| 6,364,883 B1 | 4/2002 | Santilli |
| 6,371,989 B1 | 4/2002 | Chauvin et al. |
| 6,375,682 B1 | 4/2002 | Fleischmann et al. |
| 6,379,355 B1 | 4/2002 | Zucherman et al. |
| 6,387,130 B1 | 5/2002 | Stone et al. |
| 6,395,032 B1 | 5/2002 | Gauchet et al. |
| 6,402,740 B1 | 6/2002 | Ellis et al. |
| 6,402,750 B1 | 6/2002 | Atkinson et al. |
| 6,402,784 B1 | 6/2002 | Wardlaw et al. |
| 6,413,228 B1 | 7/2002 | Hung et al. |
| 6,419,676 B1 | 7/2002 | Zucherman et al. |
| 6,419,677 B2 | 7/2002 | Zucherman et al. |
| 6,440,169 B1 | 8/2002 | Elberg et al. |
| 6,443,988 B2 | 9/2002 | Felt et al. |
| 6,447,547 B1 | 9/2002 | Michelson |
| 6,451,019 B1 * | 9/2002 | Zucherman ........ A61B 17/7062 606/249 |
| 6,451,020 B1 | 9/2002 | Zucherman et al. |
| 6,464,682 B1 | 10/2002 | Snoke |
| 6,471,976 B1 | 10/2002 | Taylor et al. |
| 6,478,796 B2 | 11/2002 | Zucherman et al. |
| 6,478,822 B1 | 11/2002 | Leroux et al. |
| 6,500,178 B2 | 12/2002 | Zucherman et al. |
| 6,514,256 B2 | 2/2003 | Zucherman et al. |
| 6,530,925 B2 | 3/2003 | Boudard et al. |
| 6,558,333 B2 | 5/2003 | Gilboa et al. |

(56) References Cited

U.S. PATENT DOCUMENTS

| | | |
|---|---|---|
| 6,565,570 B2 | 5/2003 | Sterett et al. |
| 6,572,617 B1 | 6/2003 | Senegas et al. |
| 6,575,981 B1 | 6/2003 | Boyd et al. |
| 6,579,281 B2 | 6/2003 | Palmer et al. |
| 6,579,319 B2 | 6/2003 | Goble et al. |
| 6,582,433 B2 | 6/2003 | Yun |
| 6,582,451 B1 | 6/2003 | Marucci et al. |
| 6,599,292 B1 | 7/2003 | Ray |
| 6,602,248 B1 | 8/2003 | Sharps et al. |
| 6,610,065 B1 | 8/2003 | Branch et al. |
| 6,610,091 B1 | 8/2003 | Reiley |
| 6,626,944 B1 | 9/2003 | Taylor et al. |
| 6,645,207 B2 | 11/2003 | Dixon et al. |
| 6,645,211 B2 | 11/2003 | Magana |
| 6,652,527 B2 | 11/2003 | Zucherman et al. |
| 6,652,534 B2 | 11/2003 | Zucherman et al. |
| 6,663,637 B2 | 12/2003 | Dixon et al. |
| 6,679,886 B2 | 1/2004 | Weikel et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,702,847 B2 | 3/2004 | DiCarlo |
| 6,712,819 B2 | 3/2004 | Zucherman et al. |
| 6,716,215 B1 | 4/2004 | David et al. |
| 6,716,245 B2 | 4/2004 | Pasquet et al. |
| 6,726,690 B2 | 4/2004 | Eckman |
| 6,733,534 B2 | 5/2004 | Sherman |
| 6,746,485 B1 | 6/2004 | Zucherman et al. |
| 6,761,720 B1 | 7/2004 | Senegas et al. |
| 6,783,529 B2 | 8/2004 | Hover et al. |
| 6,783,546 B2 | 8/2004 | Zucherman et al. |
| 6,796,983 B1 | 9/2004 | Zucherman et al. |
| 6,805,697 B1 | 10/2004 | Helm et al. |
| 6,835,205 B2 | 12/2004 | Atkinson et al. |
| 6,840,944 B2 | 1/2005 | Suddaby |
| 6,858,029 B2 | 2/2005 | Yeh |
| 6,869,398 B2 | 3/2005 | Obenchain et al. |
| 6,875,212 B2 | 4/2005 | Shaolian et al. |
| 6,902,566 B2 | 6/2005 | Zucherman et al. |
| 6,926,728 B2 | 8/2005 | Zucherman et al. |
| 6,946,000 B2 | 9/2005 | Senegas et al. |
| 6,949,123 B2 | 9/2005 | Reiley |
| 6,966,930 B2 | 11/2005 | Arnin et al. |
| 6,974,478 B2 | 12/2005 | Reiley et al. |
| 7,011,685 B2 | 3/2006 | Arnin et al. |
| 7,029,473 B2 | 4/2006 | Zucherman et al. |
| 7,033,358 B2 | 4/2006 | Taylor et al. |
| 7,048,736 B2 | 5/2006 | Robinson et al. |
| 7,070,598 B2 | 7/2006 | Lim et al. |
| 7,083,649 B2 | 8/2006 | Zucherman et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,101,375 B2 | 9/2006 | Zucherman et al. |
| 7,163,558 B2 | 1/2007 | Senegas et al. |
| 7,179,225 B2 | 2/2007 | Shluzas et al. |
| 7,187,064 B2 | 3/2007 | Tzu et al. |
| 7,189,234 B2 | 3/2007 | Zucherman et al. |
| 7,189,236 B2 | 3/2007 | Taylor et al. |
| 7,201,751 B2 | 4/2007 | Zucherman et al. |
| 7,217,291 B2 | 5/2007 | Zucherman et al. |
| 7,223,289 B2 | 5/2007 | Trieu et al. |
| 7,229,441 B2 | 6/2007 | Trieu et al. |
| 7,238,204 B2 | 7/2007 | Le Couedic et al. |
| 7,252,673 B2 | 8/2007 | Lim |
| 7,273,496 B2 | 9/2007 | Mitchell |
| 7,282,063 B2 | 10/2007 | Cohen et al. |
| 7,297,162 B2 | 11/2007 | Mujwid |
| 7,306,628 B2 | 12/2007 | Zucherman et al. |
| 7,318,839 B2 | 1/2008 | Malberg et al. |
| 7,320,707 B2 | 1/2008 | Zucherman et al. |
| 7,335,200 B2 | 2/2008 | Carli |
| 7,335,203 B2 | 2/2008 | Winslow et al. |
| 7,354,453 B2 | 4/2008 | McAfee |
| 7,384,340 B2 | 6/2008 | Eguchi et al. |
| 7,390,330 B2 | 6/2008 | Harp |
| 7,410,501 B2 | 8/2008 | Michelson |
| 7,442,208 B2 | 10/2008 | Mathieu et al. |
| 7,445,637 B2 | 11/2008 | Taylor |
| 7,473,268 B2 | 1/2009 | Zucherman et al. |
| 7,476,251 B2 | 1/2009 | Zucherman et al. |
| 7,481,839 B2 | 1/2009 | Zucherman et al. |
| 7,481,840 B2 | 1/2009 | Zucherman et al. |
| 7,491,204 B2 | 2/2009 | Marnay et al. |
| 7,497,859 B2 | 3/2009 | Zucherman et al. |
| 7,503,935 B2 | 3/2009 | Zucherman et al. |
| 7,504,798 B2 | 3/2009 | Kawada et al. |
| 7,510,567 B2 | 3/2009 | Zucherman et al. |
| 7,520,887 B2 | 4/2009 | Maxy et al. |
| 7,520,899 B2 | 4/2009 | Zucherman et al. |
| 7,547,308 B2 | 6/2009 | Bertagnoli et al. |
| 7,549,999 B2 | 6/2009 | Zucherman et al. |
| 7,550,009 B2 | 6/2009 | Arnin et al. |
| 7,565,259 B2 | 7/2009 | Sheng et al. |
| 7,572,276 B2 | 8/2009 | Lim et al. |
| 7,575,600 B2 | 8/2009 | Zucherman et al. |
| 7,585,313 B2 | 9/2009 | Kwak et al. |
| 7,585,316 B2 | 9/2009 | Trieu |
| 7,588,588 B2 | 9/2009 | Spitler et al. |
| 7,591,851 B2 | 9/2009 | Winslow et al. |
| 7,601,170 B2 | 10/2009 | Winslow et al. |
| 7,621,939 B2 | 11/2009 | Zucherman et al. |
| 7,635,377 B2 | 12/2009 | Zucherman et al. |
| 7,635,378 B2 | 12/2009 | Zucherman et al. |
| 7,637,950 B2 | 12/2009 | Baccelli et al. |
| 7,658,752 B2 | 2/2010 | Labrom et al. |
| 7,662,187 B2 | 2/2010 | Zucherman et al. |
| 7,666,186 B2 | 2/2010 | Harp |
| 7,666,209 B2 | 2/2010 | Zucherman et al. |
| 7,666,228 B2 | 2/2010 | Le Couedic et al. |
| 7,670,377 B2 | 3/2010 | Zucherman et al. |
| 7,682,376 B2 | 3/2010 | Trieu |
| 7,691,146 B2 | 4/2010 | Zucherman et al. |
| 7,695,513 B2 | 4/2010 | Zucherman et al. |
| 7,699,852 B2 | 4/2010 | Frankel et al. |
| 7,699,873 B2 | 4/2010 | Stevenson et al. |
| D618,796 S | 6/2010 | Cantu et al. |
| 7,727,233 B2 | 6/2010 | Blackwell et al. |
| 7,727,241 B2 | 6/2010 | Gorensek et al. |
| 7,731,751 B2 | 6/2010 | Butler et al. |
| 7,742,795 B2 | 6/2010 | Stone et al. |
| 7,749,231 B2 | 7/2010 | Bonvallet et al. |
| 7,749,252 B2 | 7/2010 | Zucherman et al. |
| 7,749,253 B2 | 7/2010 | Zucherman et al. |
| 7,753,938 B2 | 7/2010 | Aschmann et al. |
| 7,758,619 B2 | 7/2010 | Zucherman et al. |
| 7,758,647 B2 | 7/2010 | Arnin et al. |
| 7,763,028 B2 | 7/2010 | Lim et al. |
| 7,763,050 B2 | 7/2010 | Winslow et al. |
| 7,763,051 B2 | 7/2010 | Labrom et al. |
| 7,763,073 B2 | 7/2010 | Hawkins et al. |
| 7,763,074 B2 * | 7/2010 | Altarac ............. A61B 17/7065 606/90 |
| 7,766,967 B2 | 8/2010 | Francis |
| 7,776,090 B2 | 8/2010 | Winslow et al. |
| 7,780,709 B2 | 8/2010 | Bruneau et al. |
| 7,789,898 B2 | 9/2010 | Peterman |
| 7,794,476 B2 | 9/2010 | Wisnewski |
| 7,803,190 B2 | 9/2010 | Zucherman et al. |
| 7,806,911 B2 | 10/2010 | Peckham |
| 7,811,308 B2 | 10/2010 | Arnin et al. |
| 7,811,322 B2 | 10/2010 | Arnin et al. |
| 7,811,323 B2 | 10/2010 | Arnin et al. |
| 7,811,324 B2 | 10/2010 | Arnin et al. |
| 7,811,330 B2 | 10/2010 | Arnin et al. |
| 7,819,921 B2 | 10/2010 | Grotz |
| 7,828,822 B2 | 11/2010 | Zucherman et al. |
| 7,828,849 B2 | 11/2010 | Lim |
| 7,833,272 B2 | 11/2010 | Arnin et al. |
| 7,837,687 B2 | 11/2010 | Harp |
| 7,837,688 B2 | 11/2010 | Boyer, II et al. |
| 7,837,700 B2 | 11/2010 | Harp |
| 7,837,711 B2 | 11/2010 | Bruneau et al. |
| 7,837,734 B2 | 11/2010 | Zucherman et al. |

(56) References Cited

U.S. PATENT DOCUMENTS

| | | |
|---|---|---|
| 7,846,183 B2 | 12/2010 | Blain |
| 7,846,185 B2 | 12/2010 | Carls et al. |
| 7,846,186 B2 | 12/2010 | Taylor |
| 7,857,815 B2 | 12/2010 | Zucherman et al. |
| 7,862,569 B2 | 1/2011 | Zucherman et al. |
| 7,862,586 B2 | 1/2011 | Malek |
| 7,862,590 B2 | 1/2011 | Lim et al. |
| 7,862,592 B2 | 1/2011 | Peterson et al. |
| 7,862,615 B2 | 1/2011 | Carli et al. |
| 7,867,276 B2 | 1/2011 | Matge et al. |
| 7,871,426 B2 | 1/2011 | Chin et al. |
| 7,896,879 B2 | 3/2011 | Solsberg et al. |
| 7,942,830 B2 | 5/2011 | Solsberg et al. |
| 7,955,392 B2 | 6/2011 | Dewey et al. |
| 7,985,246 B2 | 7/2011 | Trieu et al. |
| 8,012,207 B2 | 9/2011 | Kim |
| 8,025,684 B2 | 9/2011 | Garcia-Bengochea et al. |
| 8,057,513 B2 | 11/2011 | Kohm et al. |
| 8,062,332 B2 | 11/2011 | Cunningham et al. |
| 8,100,823 B2 | 1/2012 | Harp |
| 8,123,782 B2 | 2/2012 | Altarac et al. |
| 8,123,807 B2 | 2/2012 | Kim |
| 8,128,662 B2 | 3/2012 | Altarac et al. |
| 8,152,837 B2 | 4/2012 | Altarac et al. |
| 8,167,944 B2 | 5/2012 | Kim |
| 8,226,690 B2 | 7/2012 | Altarac et al. |
| 8,273,108 B2 | 9/2012 | Altarac et al. |
| 8,277,488 B2 | 10/2012 | Altarac et al. |
| 8,292,922 B2 | 10/2012 | Altarac et al. |
| 8,317,864 B2 | 11/2012 | Kim |
| 8,409,282 B2 | 4/2013 | Kim |
| 8,425,559 B2 | 4/2013 | Tebbe et al. |
| 8,608,762 B2 | 12/2013 | Solsberg et al. |
| 8,613,747 B2 | 12/2013 | Altarac et al. |
| 8,628,574 B2 * | 1/2014 | Altarac ............... A61B 17/7065 606/249 |
| 8,696,671 B2 | 4/2014 | Solsberg et al. |
| 8,734,477 B2 | 5/2014 | Solsberg et al. |
| 8,740,948 B2 | 6/2014 | Reglos et al. |
| 8,845,726 B2 | 9/2014 | Tebbe et al. |
| 8,864,828 B2 | 10/2014 | Altarac et al. |
| 8,882,772 B2 | 11/2014 | Solsberg et al. |
| 8,894,653 B2 | 11/2014 | Solsberg et al. |
| 8,900,271 B2 | 12/2014 | Kim |
| 8,945,183 B2 | 2/2015 | Altarac et al. |
| 9,023,084 B2 | 5/2015 | Kim |
| 9,039,742 B2 | 5/2015 | Altarac et al. |
| 9,119,680 B2 | 9/2015 | Altarac et al. |
| 9,125,692 B2 | 9/2015 | Kim |
| 9,155,570 B2 | 10/2015 | Altarac et al. |
| 9,155,572 B2 | 10/2015 | Altarac et al. |
| 9,161,783 B2 | 10/2015 | Altarac et al. |
| 9,186,186 B2 | 11/2015 | Reglos et al. |
| 9,211,146 B2 | 12/2015 | Kim |
| 9,283,005 B2 | 3/2016 | Tebbe et al. |
| 9,314,279 B2 | 4/2016 | Kim |
| 9,393,055 B2 | 7/2016 | Altarac et al. |
| 9,445,843 B2 * | 9/2016 | Altarac ............... A61B 17/7065 |
| 2001/0031965 A1 | 10/2001 | Zucherman et al. |
| 2002/0042607 A1 | 4/2002 | Palmer et al. |
| 2002/0143331 A1 | 10/2002 | Zucherman et al. |
| 2003/0040746 A1 | 2/2003 | Mitchell et al. |
| 2003/0040753 A1 | 2/2003 | Daum et al. |
| 2003/0074075 A1 | 4/2003 | Thomas et al. |
| 2003/0149438 A1 | 8/2003 | Nichols et al. |
| 2003/0153976 A1 | 8/2003 | Cauthen et al. |
| 2003/0176921 A1 | 9/2003 | Lawson |
| 2003/0220643 A1 | 11/2003 | Ferree |
| 2003/0220650 A1 | 11/2003 | Major et al. |
| 2003/0233098 A1 | 12/2003 | Markworth |
| 2004/0087947 A1 | 5/2004 | Lim et al. |
| 2004/0106997 A1 | 6/2004 | Lieberson et al. |
| 2004/0106999 A1 | 6/2004 | Mathews et al. |
| 2004/0167625 A1 | 8/2004 | Beyar et al. |
| 2004/0220568 A1 | 11/2004 | Zucherman et al. |
| 2005/0049708 A1 | 3/2005 | Atkinson et al. |
| 2005/0075634 A1 | 4/2005 | Zucherman et al. |
| 2005/0090822 A1 | 4/2005 | DiPoto et al. |
| 2005/0101955 A1 | 5/2005 | Zucherman et al. |
| 2005/0125066 A1 | 6/2005 | McAfee |
| 2005/0143738 A1 | 6/2005 | Zucherman et al. |
| 2005/0165398 A1 | 7/2005 | Reiley |
| 2005/0192586 A1 | 9/2005 | Zucherman et al. |
| 2005/0192671 A1 | 9/2005 | Bao et al. |
| 2005/0209603 A1 | 9/2005 | Zucherman et al. |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0228426 A1 | 10/2005 | Campbell |
| 2005/0245937 A1 | 11/2005 | Winslow |
| 2005/0278028 A1 * | 12/2005 | Mujwid ............... A61F 2/446 623/17.13 |
| 2005/0278036 A1 | 12/2005 | Leonard et al. |
| 2006/0036258 A1 | 2/2006 | Zucherman et al. |
| 2006/0064165 A1 | 3/2006 | Zucherman et al. |
| 2006/0064166 A1 | 3/2006 | Zucherman et al. |
| 2006/0074431 A1 | 4/2006 | Sutton et al. |
| 2006/0084976 A1 | 4/2006 | Borgstrom et al. |
| 2006/0084983 A1 | 4/2006 | Kim |
| 2006/0084985 A1 | 4/2006 | Kim |
| 2006/0084988 A1 | 4/2006 | Kim |
| 2006/0084991 A1 | 4/2006 | Borgstrom et al. |
| 2006/0085069 A1 | 4/2006 | Kim |
| 2006/0085070 A1 | 4/2006 | Kim |
| 2006/0085074 A1 | 4/2006 | Raiszadeh |
| 2006/0089718 A1 | 4/2006 | Zucherman et al. |
| 2006/0102269 A1 | 5/2006 | Uchida et al. |
| 2006/0122620 A1 | 6/2006 | Kim |
| 2006/0149254 A1 | 7/2006 | Lauryssen et al. |
| 2006/0149289 A1 | 7/2006 | Winslow et al. |
| 2006/0167416 A1 | 7/2006 | Mathis et al. |
| 2006/0195102 A1 * | 8/2006 | Malandain ............ A61B 17/025 606/86 A |
| 2006/0217811 A1 | 9/2006 | Lambrecht et al. |
| 2006/0224159 A1 | 10/2006 | Anderson |
| 2006/0235386 A1 | 10/2006 | Anderson |
| 2006/0241597 A1 | 10/2006 | Mitchell et al. |
| 2006/0241614 A1 | 10/2006 | Bruneau et al. |
| 2006/0241757 A1 | 10/2006 | Anderson |
| 2006/0247623 A1 * | 11/2006 | Anderson ........... A61B 17/7062 606/248 |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0247773 A1 | 11/2006 | Stamp |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271044 A1 | 11/2006 | Petrini et al. |
| 2006/0271049 A1 | 11/2006 | Zucherman et al. |
| 2006/0271055 A1 | 11/2006 | Thramann |
| 2006/0271061 A1 | 11/2006 | Beyar et al. |
| 2006/0271194 A1 | 11/2006 | Zucherman et al. |
| 2006/0276801 A1 | 12/2006 | Yerby et al. |
| 2006/0276897 A1 | 12/2006 | Winslow et al. |
| 2006/0282077 A1 | 12/2006 | Labrom et al. |
| 2006/0282078 A1 | 12/2006 | Labrom et al. |
| 2007/0016196 A1 | 1/2007 | Winslow et al. |
| 2007/0055237 A1 | 3/2007 | Edidin et al. |
| 2007/0055246 A1 | 3/2007 | Zucherman et al. |
| 2007/0073289 A1 | 3/2007 | Kwak et al. |
| 2007/0100340 A1 | 5/2007 | Lange et al. |
| 2007/0100366 A1 | 5/2007 | Dziedzic et al. |
| 2007/0123863 A1 | 5/2007 | Winslow et al. |
| 2007/0123904 A1 | 5/2007 | Stad et al. |
| 2007/0161991 A1 | 7/2007 | Altarac et al. |
| 2007/0161993 A1 | 7/2007 | Lowery et al. |
| 2007/0173818 A1 | 7/2007 | Hestad et al. |
| 2007/0173821 A1 | 7/2007 | Trieu |
| 2007/0173822 A1 | 7/2007 | Bruneau et al. |
| 2007/0173823 A1 | 7/2007 | Dewey et al. |
| 2007/0173832 A1 | 7/2007 | Tebbe et al. |
| 2007/0173939 A1 | 7/2007 | Kim et al. |

(56) References Cited

U.S. PATENT DOCUMENTS

| | | |
|---|---|---|
| 2007/0179500 A1 | 8/2007 | Chin et al. |
| 2007/0185490 A1 | 8/2007 | Implicit |
| 2007/0191948 A1 | 8/2007 | Arnin et al. |
| 2007/0191991 A1 | 8/2007 | Addink |
| 2007/0198045 A1 | 8/2007 | Morton et al. |
| 2007/0198091 A1 | 8/2007 | Boyer et al. |
| 2007/0203493 A1 | 8/2007 | Zucherman et al. |
| 2007/0203495 A1 | 8/2007 | Zucherman et al. |
| 2007/0203496 A1 | 8/2007 | Zucherman et al. |
| 2007/0203497 A1 | 8/2007 | Zucherman et al. |
| 2007/0203501 A1 | 8/2007 | Zucherman et al. |
| 2007/0208345 A1 | 9/2007 | Marnay et al. |
| 2007/0208346 A1 | 9/2007 | Marnay et al. |
| 2007/0208366 A1 | 9/2007 | Pellegrino et al. |
| 2007/0210018 A1 | 9/2007 | Wallwiener et al. |
| 2007/0225706 A1 | 9/2007 | Clark et al. |
| 2007/0225724 A1 | 9/2007 | Edmond |
| 2007/0225807 A1 | 9/2007 | Phan et al. |
| 2007/0225814 A1 | 9/2007 | Atkinson et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233077 A1 | 10/2007 | Khalili |
| 2007/0233081 A1 | 10/2007 | Pasquet et al. |
| 2007/0233082 A1 | 10/2007 | Chin et al. |
| 2007/0233083 A1 | 10/2007 | Abdou |
| 2007/0233084 A1 | 10/2007 | Betz et al. |
| 2007/0233088 A1 | 10/2007 | Edmond |
| 2007/0233089 A1 | 10/2007 | DiPoto et al. |
| 2007/0233096 A1 | 10/2007 | Garcia-Bengochea |
| 2007/0233098 A1 | 10/2007 | Mastrorio et al. |
| 2007/0233129 A1 | 10/2007 | Bertagnoli et al. |
| 2007/0250060 A1 | 10/2007 | Anderson et al. |
| 2007/0260245 A1 | 11/2007 | Malandain et al. |
| 2007/0265623 A1 | 11/2007 | Malandain et al. |
| 2007/0265624 A1 | 11/2007 | Zucherman et al. |
| 2007/0265625 A1 | 11/2007 | Zucherman et al. |
| 2007/0265626 A1 | 11/2007 | Seme |
| 2007/0270822 A1 | 11/2007 | Heinz |
| 2007/0270823 A1 | 11/2007 | Trieu et al. |
| 2007/0270824 A1 | 11/2007 | Lim et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276372 A1 | 11/2007 | Malandain et al. |
| 2007/0276373 A1 | 11/2007 | Malandain |
| 2007/0276390 A1 | 11/2007 | Solsberg et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0276500 A1 | 11/2007 | Zucherman et al. |
| 2008/0015700 A1 | 1/2008 | Zucherman et al. |
| 2008/0021468 A1 | 1/2008 | Zucherman et al. |
| 2008/0021560 A1 | 1/2008 | Zucherman et al. |
| 2008/0021561 A1 | 1/2008 | Zucherman et al. |
| 2008/0027545 A1 | 1/2008 | Zucherman et al. |
| 2008/0027552 A1 | 1/2008 | Zucherman et al. |
| 2008/0027553 A1 | 1/2008 | Zucherman et al. |
| 2008/0033445 A1 | 2/2008 | Zucherman et al. |
| 2008/0033553 A1 | 2/2008 | Zucherman et al. |
| 2008/0033558 A1 | 2/2008 | Zucherman et al. |
| 2008/0033559 A1 | 2/2008 | Zucherman et al. |
| 2008/0039853 A1 | 2/2008 | Zucherman et al. |
| 2008/0039858 A1 | 2/2008 | Zucherman et al. |
| 2008/0039859 A1 | 2/2008 | Zucherman et al. |
| 2008/0039945 A1 | 2/2008 | Zucherman et al. |
| 2008/0039946 A1 | 2/2008 | Zucherman et al. |
| 2008/0039947 A1 | 2/2008 | Zucherman et al. |
| 2008/0045958 A1 | 2/2008 | Zucherman et al. |
| 2008/0045959 A1 | 2/2008 | Zucherman et al. |
| 2008/0046081 A1 | 2/2008 | Zucherman et al. |
| 2008/0046085 A1 | 2/2008 | Zucherman et al. |
| 2008/0046086 A1 | 2/2008 | Zucherman et al. |
| 2008/0046087 A1 | 2/2008 | Zucherman et al. |
| 2008/0046088 A1 | 2/2008 | Zucherman et al. |
| 2008/0051785 A1 | 2/2008 | Zucherman et al. |
| 2008/0051898 A1 | 2/2008 | Zucherman et al. |
| 2008/0051899 A1 | 2/2008 | Zucherman et al. |
| 2008/0051904 A1 | 2/2008 | Zucherman et al. |
| 2008/0051905 A1 | 2/2008 | Zucherman et al. |
| 2008/0058806 A1 | 3/2008 | Klyce et al. |
| 2008/0058807 A1 | 3/2008 | Klyce et al. |
| 2008/0058808 A1 | 3/2008 | Klyce et al. |
| 2008/0058941 A1 | 3/2008 | Zucherman et al. |
| 2008/0065086 A1 | 3/2008 | Zucherman et al. |
| 2008/0065212 A1 | 3/2008 | Zucherman et al. |
| 2008/0065213 A1 | 3/2008 | Zucherman et al. |
| 2008/0065214 A1 | 3/2008 | Zucherman et al. |
| 2008/0071280 A1 | 3/2008 | Winslow |
| 2008/0071378 A1 | 3/2008 | Zucherman et al. |
| 2008/0086212 A1 | 4/2008 | Zucherman et al. |
| 2008/0108990 A1 | 5/2008 | Mitchell et al. |
| 2008/0114455 A1 | 5/2008 | Lange et al. |
| 2008/0132952 A1 | 6/2008 | Malandain et al. |
| 2008/0167655 A1 | 7/2008 | Wang et al. |
| 2008/0167656 A1 | 7/2008 | Zucherman et al. |
| 2008/0172057 A1 | 7/2008 | Zucherman et al. |
| 2008/0177272 A1 | 7/2008 | Zucherman et al. |
| 2008/0177306 A1 | 7/2008 | Lamborne et al. |
| 2008/0177312 A1 | 7/2008 | Perez-Cruet et al. |
| 2008/0183210 A1 | 7/2008 | Zucherman et al. |
| 2008/0188895 A1 | 8/2008 | Cragg et al. |
| 2008/0208344 A1 | 8/2008 | Kilpela et al. |
| 2008/0215058 A1 | 9/2008 | Zucherman et al. |
| 2008/0221692 A1 | 9/2008 | Zucherman et al. |
| 2008/0228225 A1 | 9/2008 | Trautwein et al. |
| 2008/0234708 A1 | 9/2008 | Houser et al. |
| 2008/0234824 A1 | 9/2008 | Youssef et al. |
| 2008/0288075 A1 | 11/2008 | Zucherman et al. |
| 2008/0319550 A1 | 12/2008 | Altarac et al. |
| 2009/0012528 A1 | 1/2009 | Aschmann et al. |
| 2009/0118833 A1 | 5/2009 | Hudgins et al. |
| 2009/0125030 A1 | 5/2009 | Tebbe et al. |
| 2009/0125036 A1 | 5/2009 | Bleich |
| 2009/0138046 A1 | 5/2009 | Altarac et al. |
| 2009/0138055 A1 | 5/2009 | Altarac et al. |
| 2009/0222043 A1 | 9/2009 | Altarac et al. |
| 2009/0248079 A1 | 10/2009 | Kwak et al. |
| 2009/0292315 A1 | 11/2009 | Trieu |
| 2010/0042217 A1 | 2/2010 | Zucherman et al. |
| 2010/0082108 A1 | 4/2010 | Zucherman et al. |
| 2010/0114100 A1 | 5/2010 | Mehdizade |
| 2010/0131009 A1 | 5/2010 | Roebling et al. |
| 2010/0228092 A1 | 9/2010 | Ortiz et al. |
| 2010/0234889 A1 | 9/2010 | Hess |
| 2010/0262243 A1 | 10/2010 | Zucherman et al. |
| 2010/0280551 A1 | 11/2010 | Pool et al. |
| 2010/0305611 A1 | 12/2010 | Zucherman et al. |
| 2011/0245833 A1 | 10/2011 | Anderson |
| 2011/0313457 A1 | 12/2011 | Reglos et al. |
| 2012/0078301 A1 | 3/2012 | Hess |
| 2012/0158063 A1 | 6/2012 | Altarac et al. |
| 2012/0226315 A1 | 9/2012 | Altarac et al. |
| 2012/0232552 A1 | 9/2012 | Morgenstern Lopez et al. |
| 2012/0303039 A1 | 11/2012 | Chin et al. |
| 2012/0330359 A1 | 12/2012 | Kim |
| 2013/0012998 A1 | 1/2013 | Altarac et al. |
| 2013/0072985 A1 | 3/2013 | Kim |
| 2013/0150886 A1 | 6/2013 | Altarac et al. |
| 2013/0165974 A1 | 6/2013 | Kim |
| 2013/0165975 A1 | 6/2013 | Tebbe et al. |
| 2013/0172932 A1 | 7/2013 | Altarac et al. |
| 2013/0172933 A1 | 7/2013 | Altarac et al. |
| 2013/0289399 A1 | 10/2013 | Choi et al. |
| 2013/0289622 A1 | 10/2013 | Kim |
| 2014/0081332 A1 | 3/2014 | Altarac et al. |
| 2014/0214082 A1 | 7/2014 | Reglos et al. |
| 2014/0275992 A1 | 9/2014 | Choi et al. |
| 2015/0150598 A1 | 6/2015 | Tebbe et al. |

(56) References Cited

U.S. PATENT DOCUMENTS

| | | |
|---|---|---|
| 2015/0150604 A1 | 6/2015 | Kim |
| 2015/0164560 A1 | 6/2015 | Altarac et al. |
| 2015/0374415 A1 | 12/2015 | Kim |
| 2016/0030092 A1 | 2/2016 | Altarac et al. |
| 2016/0045232 A1 | 2/2016 | Altarac et al. |
| 2016/0066963 A1 | 3/2016 | Kim |
| 2016/0135853 A1 | 5/2016 | Altarac et al. |
| 2016/0248222 A1 | 8/2016 | Miyata |
| 2016/0317193 A1 | 11/2016 | Kim et al. |

FOREIGN PATENT DOCUMENTS

| | | |
|---|---|---|
| CN | 101897603 | 12/2010 |
| DE | 69507480 | 9/1999 |
| EP | 322334 | 6/1989 |
| EP | 0767636 | 4/1997 |
| EP | 0768843 B1 | 4/1997 |
| EP | 0959792 B1 | 12/1999 |
| EP | 1027004 A1 | 8/2000 |
| EP | 1030615 A1 | 8/2000 |
| EP | 1138268 | 10/2001 |
| EP | 1330987 A1 | 7/2003 |
| EP | 1056408 B1 | 12/2003 |
| EP | 1343424 B1 | 9/2004 |
| EP | 1454589 A1 | 9/2004 |
| EP | 1148850 B1 | 4/2005 |
| EP | 1570793 A2 | 9/2005 |
| EP | 1299042 B1 | 3/2006 |
| EP | 1578314 B1 | 5/2007 |
| EP | 1675535 B1 | 5/2007 |
| EP | 1861046 A2 | 12/2007 |
| FR | 2681525 A1 | 3/1993 |
| FR | 2722980 A1 | 2/1996 |
| FR | 2816197 A1 | 5/2002 |
| FR | 2884136 A1 | 10/2006 |
| FR | 2888744 A1 | 1/2007 |
| SU | 988281 A1 | 1/1983 |
| WO | WO-9404088 A1 | 3/1994 |
| WO | WO-9426192 A1 | 11/1994 |
| WO | WO-9525485 A1 | 9/1995 |
| WO | WO-9531158 A1 | 11/1995 |
| WO | WO-9600049 A1 | 1/1996 |
| WO | WO-9829047 A1 | 7/1998 |
| WO | WO-9921500 A1 | 5/1999 |
| WO | WO-9921501 A1 | 5/1999 |
| WO | WO-9942051 A1 | 8/1999 |
| WO | WO-0013619 A1 | 3/2000 |
| WO | WO-0044319 A1 | 8/2000 |
| WO | WO-0044321 A2 | 8/2000 |
| WO | WO-0128442 A1 | 4/2001 |
| WO | WO-0191657 A1 | 12/2001 |
| WO | WO-0191658 A1 | 12/2001 |
| WO | WO-0203882 A2 | 1/2002 |
| WO | WO-0207623 A1 | 1/2002 |
| WO | WO-0207624 A1 | 1/2002 |
| WO | WO-02051326 A1 | 7/2002 |
| WO | WO-02067793 A2 | 9/2002 |
| WO | WO-02071960 A1 | 9/2002 |
| WO | WO-02076336 A2 | 10/2002 |
| WO | WO-03007791 A2 | 1/2003 |
| WO | WO-03007829 A1 | 1/2003 |
| WO | WO-03008016 A2 | 1/2003 |
| WO | WO-03015646 A2 | 2/2003 |
| WO | WO-03024298 A2 | 3/2003 |
| WO | WO-03045262 A2 | 6/2003 |
| WO | WO-03099147 A1 | 12/2003 |
| WO | WO-03101350 A1 | 12/2003 |
| WO | WO-04073533 A1 | 9/2004 |
| WO | WO-04110300 A2 | 12/2004 |
| WO | WO-05009300 A1 | 2/2005 |
| WO | WO-05013839 A2 | 2/2005 |
| WO | WO-05025461 A2 | 3/2005 |
| WO | WO-05041799 A1 | 5/2005 |
| WO | WO-05044152 A1 | 5/2005 |
| WO | WO-05055868 A2 | 6/2005 |
| WO | WO-05079672 A2 | 9/2005 |
| WO | WO-2005086776 A2 | 9/2005 |
| WO | WO-05115261 A1 | 12/2005 |
| WO | WO-06033659 A2 | 3/2006 |
| WO | WO-06034423 A2 | 3/2006 |
| WO | WO-06039243 | 4/2006 |
| WO | WO-06039260 A2 | 4/2006 |
| WO | WO-06045094 A2 | 4/2006 |
| WO | WO-2006045094 A2 | 4/2006 |
| WO | WO-06063047 A2 | 6/2006 |
| WO | WO-06065774 A1 | 6/2006 |
| WO | WO-2006063047 A2 | 6/2006 |
| WO | WO-2006064356 A1 | 6/2006 |
| WO | WO-2006089085 A2 | 8/2006 |
| WO | WO-06102269 A2 | 9/2006 |
| WO | WO-06102428 A1 | 9/2006 |
| WO | WO-06102485 A2 | 9/2006 |
| WO | WO-06107539 A1 | 10/2006 |
| WO | WO-06110462 A2 | 10/2006 |
| WO | WO-06110464 A1 | 10/2006 |
| WO | WO-06110767 A1 | 10/2006 |
| WO | WO-06113080 A2 | 10/2006 |
| WO | WO-06113406 A2 | 10/2006 |
| WO | WO-06113814 A2 | 10/2006 |
| WO | WO-06118945 A1 | 11/2006 |
| WO | WO-06119235 A1 | 11/2006 |
| WO | WO-06119236 A2 | 11/2006 |
| WO | WO-06135511 A1 | 12/2006 |
| WO | WO-07015028 A1 | 2/2007 |
| WO | WO-07035120 A2 | 3/2007 |
| WO | WO-07075375 A2 | 7/2007 |
| WO | WO-07075788 A2 | 7/2007 |
| WO | WO-07075791 A2 | 7/2007 |
| WO | WO-07089605 A2 | 8/2007 |
| WO | WO-07089905 A2 | 8/2007 |
| WO | WO-07089975 A1 | 8/2007 |
| WO | WO-07097735 A2 | 8/2007 |
| WO | WO-07109402 A2 | 9/2007 |
| WO | WO-07110604 A1 | 10/2007 |
| WO | WO-07111795 A1 | 10/2007 |
| WO | WO-07111979 A2 | 10/2007 |
| WO | WO-07111999 A2 | 10/2007 |
| WO | WO-07117882 A1 | 10/2007 |
| WO | WO-07121070 A2 | 10/2007 |
| WO | WO-07127550 A2 | 11/2007 |
| WO | WO-07127588 A1 | 11/2007 |
| WO | WO-07127677 A1 | 11/2007 |
| WO | WO-07127689 A2 | 11/2007 |
| WO | WO-07127694 A2 | 11/2007 |
| WO | WO-07127734 A2 | 11/2007 |
| WO | WO-07127736 A2 | 11/2007 |
| WO | WO-07131165 A2 | 11/2007 |
| WO | WO-07134113 A2 | 11/2007 |
| WO | WO-2008009049 A1 | 1/2008 |
| WO | WO-08048645 A2 | 4/2008 |
| WO | WO-2008057506 A2 | 5/2008 |
| WO | WO-2008130564 A1 | 10/2008 |
| WO | WO-2009014728 A2 | 1/2009 |
| WO | WO-2009033093 A1 | 3/2009 |
| WO | WO-2009086010 A2 | 7/2009 |
| WO | WO-2009091922 A2 | 7/2009 |
| WO | WO-2009094463 A2 | 7/2009 |
| WO | WO-2009114479 A2 | 9/2009 |
| WO | WO-2011084477 A2 | 7/2011 |
| WO | WO-2015171814 A1 | 11/2015 |

OTHER PUBLICATIONS

Choi, Gun et al., "Percutaneous Endoscopic Interlaminar Disectomy for Intracanalicular Disc Herniations at L5-S1 Using a Rigid Working Channel Endoscope," Operative Neurosurg., 58: pp. 59-68 (2006).

Decision on Petition in U.S. Appl. No. 60/592,099, May 4, 2005.

Fast, Avital et al., "Surgical Treatment of Lumbar Spinal Stenosis in the Elderly," Arch Phys. Med Rehabil., Mar. 1985, pp. 149-151, vol. 66.

(56) References Cited

OTHER PUBLICATIONS

Lee, Seungcheol et al., "New Surgical Techniques of Percutaneous Endoscopic Lumbar Disectomy for Migrated Disc Herniation," Joint Dis. Rel. Surg., 16(2); pp. 102-110 (2005).
Lee, Seungcheol et al., "Percutaneous Endoscopic Interlaminar Disectomy for L5-S1 Disc Herniation: Axillary Approach and Preliminary Results," J. of Korean Neurosurg. Soc., 40: pp. 19-83 (2006).
McCulloch, John A., Young, Paul H., "Essentials of Spinal Microsurgery," 1998, pp. 453-485. Lippincott-Raven Publishers, Philadelphia, PA (37 pages total).
Minns, R.J., et al., "Preliminary Design and Experimental Studies of a Noval Soft Implant for Correcting Sagittal Plane Instability in the Lumbar Spine," (1997) Spine, 22(16): 1819-1827.
Palmer, Sylvain et al., "Bilateral decompressive surgery in lumbar spinal stenosis associated with spondylolisthesis: unilateral approach and use of a microscope and tubular retractor system," Neurosurgery Focus, Jul. 2002, pp. 1-6, vol. 13.
Swan, Colby, "Preliminary Design and Experimental Studies of a Novel Soft Implant for Correcting Sogittal Plane Instability in the Lumbar Spine," Spine, 1997, 22(16), 1826-1827.
Tredway, Trent L. et al., "Minimally Invasive Transforaminal Lumbar Interbody Fusion (MI-TLIF) and Lateral Mass Fusion with the MetRx System," (14 pages total), 2005.
Vaccaro, Alexander J. et al., MasterCases Spine Surgery, 2001, pp. 100-107. Thieme Medical Publishers, Inc., NY. (10 pages total).
Vertos Mild Devices Kit—PRT-00430-C—Instructions for Use (13 pages total); see http://vertosmed.com/docs/mildIFU_PRT-00430-C.pdf., 2012.

\* cited by examiner

SYSTEMS AND METHODS FOR POSTERIOR DYNAMIC STABILIZATION OF THE SPINE

CROSS-REFERENCE TO RELATED APPLICATIONS

This application is a continuation of U.S. patent application Ser. No. 14/154,094, filed on Jan. 13, 2014, which is a continuation of U.S. patent application No. of Ser. No. 12/844,365, filed Jul. 27, 2010, now U.S. Pat. No. 8,628,574, which is a continuation of U.S. patent application Ser. No. 11/305,820, filed Dec. 15, 2005, now U.S. Pat. No. 7,763,074, which is a continuation-in-part of U.S. patent application Ser. No. 11/190,496, filed Jul. 26, 2005, now U.S. Pat. No. 8,409,282, which is a continuation-in-part of U.S. patent application Ser. No. 11/079,006, filed on Mar. 10, 2005, now U.S. Pat. No. 8,012,207, which is a continuation-in-part of U.S. patent application Ser. No. 11/052,002, filed Feb. 4, 2005, now U.S. Pat. No. 8,317,864, which is a continuation-in-part of U.S. patent application Ser. No. 11/006,502, filed on Dec. 6, 2004, now U.S. Pat. No. 8,123,807, which is a continuation-in-part of U.S. patent application Ser. No. 10/970,843, filed Oct. 20, 2004, now U.S. Pat. No. 8,167,944, all of which are hereby incorporated by reference in their entireties.

FIELD OF THE INVENTION

The present invention is directed towards the treatment of spinal disorders and pain. More particularly, the present invention is directed to systems and methods of treating the spine, which eliminate pain and enable spinal motion, which effectively mimics that of a normally functioning spine.

BACKGROUND OF THE INVENTION

FIG. 1 illustrates a portion of the human spine having a superior vertebra 2 and an inferior vertebra 4, with an intervertebral disc 6 located in between the two vertebral bodies. The superior vertebra 2 has superior facet joints 8a and 8b, inferior facet joints 13a and 13b, and spinous process 25. Pedicles 3a and 3b interconnect the respective superior facet joints 8a, 8b to the vertebral body 2. Extending laterally from superior facet joints 8a, 8b are transverse processes 7a and 7b, respectively. Extending between each inferior facet joints 13a and 13b and the spinous process 25 are laminal zones 5a and 5b, respectively. Similarly, inferior vertebra 4 has superior facet joints 15a and 15b, superior pedicles 9a and 9b, transverse processes 17a and 17b, inferior facet joints 19a and 19b, laminal zones 21a and 21b, and spinous process 27.

The superior vertebra with its inferior facets, the inferior vertebra with its superior facet joints, the intervertebral disc, and seven spinal ligaments (not shown) extending between the superior and inferior vertebrae together comprise a spinal motion segment or functional spine unit. Each spinal motion segment enables motion along three orthogonal axes, both in rotation and in translation. The various spinal motions are illustrated in FIGS. 2A-2C. In particular, FIG. 2A illustrates flexion and extension motions and axial loading, FIG. 2B illustrates lateral bending motion and FIG. 2C illustrated axial rotational motion. A normally functioning spinal motion segment provides physiological limits and stiffness in each rotational and translational direction to create a stable and strong column structure to support physiological loads.

Traumatic, inflammatory, metabolic, synovial, neoplastic and degenerative disorders of the spine can produce debilitating pain that can affect a spinal motion segment's ability to properly function. The specific location or source of spinal pain is most often an affected intervertebral disc or facet joint. Often, a disorder in one location or spinal component can lead to eventual deterioration or disorder, and ultimately, pain in the other.

Spine fusion (arthrodesis) is a procedure in which two or more adjacent vertebral bodies are fused together. It is one of the most common approaches to alleviating various types of spinal pain, particularly pain associated with one or more affected intervertebral discs. While spine fusion generally helps to eliminate certain types of pain, it has been shown to decrease function by limiting the range of motion for patients in flexion, extension, rotation and lateral bending. Furthermore, the fusion creates increased stresses on adjacent non-fused motion segments and accelerated degeneration of the motion segments. Additionally, pseudarthrosis (resulting from an incomplete or ineffective fusion) may not provide the expected pain-relief for the patient. Also, the device(s) used for fusion, whether artificial or biological, may migrate out of the fusion site creating significant new problems for the patient.

Various technologies and approaches have been developed to treat spinal pain without fusion in order to maintain or recreate the natural biomechanics of the spine. To this end, significant efforts are being made in the use of implantable artificial intervertebral discs. Artificial discs are intended to restore articulation between vertebral bodies so as to recreate the full range of motion normally allowed by the elastic properties of the natural disc. Unfortunately, the currently available artificial discs do not adequately address all of the mechanics of motion for the spinal column.

It has been found that the facet joints can also be a significant source of spinal disorders and debilitating pain. For example, a patient may suffer from arthritic facet joints, severe facet joint tropism, otherwise deformed facet joints, facet joint injuries, etc. These disorders lead to spinal stenosis, degenerative spondylolithesis, and/or isthmic spondylotlisthesis, pinching the nerves that extend between the affected vertebrae.

Current interventions for the treatment of facet joint disorders have not been found to provide completely successful results. Facetectomy (removal of the facet joints) may provide some pain relief but as the facet joints help to support axial, torsional, and shear loads that act on the spinal column in addition to providing a sliding articulation and mechanism for load transmission, their removal inhibits natural spinal function. Laminectomy (removal of the lamina, including the spinal arch and the spinous process) may also provide pain relief associated with facet joint disorders; however, the spine is made less stable and subject to hypermobility. Problems with the facet joints can also complicate treatments associated with other portions of the spine. In fact, contraindications for disc replacement include arthritic facet joints, absent facet joints, severe facet joint tropism, or otherwise deformed facet joints due to the inability of the artificial disc (when used with compromised or missing facet joints) to properly restore the natural biomechanics of the spinal motion segment.

While various attempts have been made at facet joint replacement, they have been inadequate. This is due to the fact that prosthetic facet joints preserve existing bony structures and therefore do not address pathologies that affect facet joints themselves. Certain facet joint prostheses, such as those disclosed in U.S. Pat. No. 6,132,464, are intended to be supported on the lamina or the posterior arch. As the lamina is a very complex and highly variable anatomical structure, it is very difficult to design a prosthesis that provides reproducible positioning against the lamina to correctly locate the prosthetic facet joints. In addition, when facet joint replacement involves complete removal and replacement of the natural facet joint, as disclosed in U.S. Pat. No. 6,579,319, the prosthesis is unlikely to endure the loads and cycling experienced by the vertebra. Thus, the facet joint replacement may be subject to long-term displacement. Furthermore, when facet joint disorders are accompanied by disease or trauma to other structures of a vertebra (such as the lamina, spinous process, and/or transverse processes) facet joint replacement is insufficient to treat the problem(s).

Most recently, surgical-based technologies, referred to as "dynamic posterior stabilization," have been developed to address spinal pain resulting from more than one disorder, when more than one structure of the spine have been compromised. An objective of such technologies is to provide the support of fusion-based implants while maximizing the natural biomechanics of the spine. Dynamic posterior stabilization systems typically fall into one of two general categories: posterior pedicle screw-based systems and interspinous spacers.

Examples of pedicle screw-based systems are disclosed in U.S. Pat. Nos. 5,015,247, 5,484,437, 5,489,308, 5,609,636 and 5,658,337, 5,741,253, 6,080,155, 6,096,038, 6,264,656 and 6,270,498. These types of systems involve the use of screws that are positioned in the vertebral body through the pedicle. Certain types of these pedicle screw-based systems may be used to augment compromised facet joints, while others require removal of the spinous process and/or the facet joints for implantation. One such system, the Zimmer Spine Dynesys® employs a cord which is extended between the pedicle screws and a fairly rigid spacer which is passed over the cord and positioned between the screws. While this system is able to provide load sharing and restoration of disc height, because it is so rigid, it does not effective in preserving the natural motion of the spinal segment into which it is implanted. Other pedicle screw-based systems employ articulating joints between the pedicle screws. Because these types of systems require the use of pedicle screws, implantation of the systems are often more invasive to implant than interspinous spacers.

Where the level of disability or pain to the affected spinal motion segments is not that severe or where the condition, such as an injury, is not chronic, the use of interspinous spacers are preferred over pedicle based systems as they require a less invasive implantation approach and less dissection of the surrounding tissue and ligaments. Examples of interspinous spacers are disclosed in U.S. Pat. Nos. Re. 36,211, U.S. Pat. Nos. 5,645,599, 6,149,642, 6,500,178, 6,695,842, 6,716,245 and 6,761,720. The spacers, which are made of either a hard or compliant material, are placed in between adjacent spinous processes. The harder material spacers are fixed in place by means of the opposing force caused by distracting the affected spinal segment and/or by use of keels or screws that anchor into the spinous process. While slightly less invasive than the procedures required for implanting a pedicle screw-based dynamic stabilization system, implantation of hard or solid interspinous spacers still requires dissection of muscle tissue and of the supraspinous and interspinous ligaments. Additionally, these tend to facilitate spinal motion that is less analogous to the natural spinal motion than do the more compliant and flexible interspinous spacers. Another advantage of the compliant/flexible interspinous spacers is the ability to deliver them somewhat less invasively than those that are not compliant or flexible; however, their compliancy makes them more susceptible to displacement or migration over time. To obviate this risk, many of these spacers employ straps or the like that are wrapped around the spinous processes of the vertebrae above and below the level where the spacer is implanted. Of course, this requires some additional tissue and ligament dissection superior and inferior to the implant site, i.e., at least within the adjacent interspinous spaces.

With the limitations of current spine stabilization technologies, there is clearly a need for an improved means and method for dynamic posterior stabilization of the spine that address the drawbacks of prior devices. In particular, it would be highly beneficial to have a dynamic stabilization system that involves a minimally invasive implantation procedure, where the extent of distraction between the affected vertebrae is adjustable upon implantation and at a later time if necessary. It would be additionally advantageous if the system or device was also removable in a minimally invasive manner.

SUMMARY OF THE INVENTION

The present invention provides devices, systems and methods for stabilizing at least one spinal motion segment. The stabilizing devices include an expandable spacer or member having an unexpanded configuration and an expanded configuration, wherein the expandable member in an expanded configuration has a size, volume, diameter, length, cross-section and/or shape configured for positioning between the spinous processes of adjacent vertebrae in order to distract the vertebrae relative to each other.

In certain embodiments, the expandable member is a helical body having a varying cross-section along its longitudinal axis, such that compression, squeezing, or other longitudinal translation of the helical body causes the helical body to expand in at least one direction. When placed between two spinous processes, the expansion allows support and stabilization of the processes relative to each other.

The stabilizing devices may be configured such that the transformation from the low-profile state to the high-profile state is immediate or gradual, where the extent of expansion is controllable. The transformation may occur in one-step or evolve in continuous fashion where at least one of volume, shape, size, diameter, length, etc. is continually changing until the desired expansion end point is achieved. This transformation may be reversible such that after implantation, the stabilizing device may be partially or completely unexpanded, collapsed, deflated or at least reduced in size, volume, etc. in order to facilitate removal of the member from the implant site or to facilitate adjustment or repositioning of the member in vivo.

The stabilizing devices may be configured to stay stationary in the implant site on their own (or "float") or may be further fixed or anchored to surrounding tissue, e.g., bone (e.g., spinous processes, vertebrae), muscle, ligaments or other soft tissue, to ensure against migration of the implant. In their final deployed state, the stabilizing devices may be flexible to allow some degree of extension of the spine or may otherwise be rigid so as prevent extension altogether. Optionally, the devices may include one or more markers on a surface of the expandable member to facilitate fluoroscopic imaging.

The invention further includes methods for stabilizing at least one spinal motion segment which involve the implantation of one or more devices or expandable spacers of the present invention, in which the expandable member is positioned between the spinous processes of adjacent vertebrae in an unexpanded or undeployed condition and then subsequently expanded or deployed to a size and/or shape for selectively distracting the adjacent vertebrae. The invention also contemplates the temporary implantation of the subject devices which may be subsequently removed from the patient once the intended treatment is complete. The methods may also include adjustment of the implants in vivo.

Many of the methods involve the percutaneous implantation of the subject devices from either an ipsolateral approach or a mid-line approach into the interspinous space. Certain methods involve the delivery of certain components by a lateral approach and other components by a mid-line approach. The implantation methods may involve the use of cannulas through which the stabilizing devices are delivered into an implant site, however, such may not be required, with the stabilizing devices be configured to pass directly through an incision.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Figure 1:
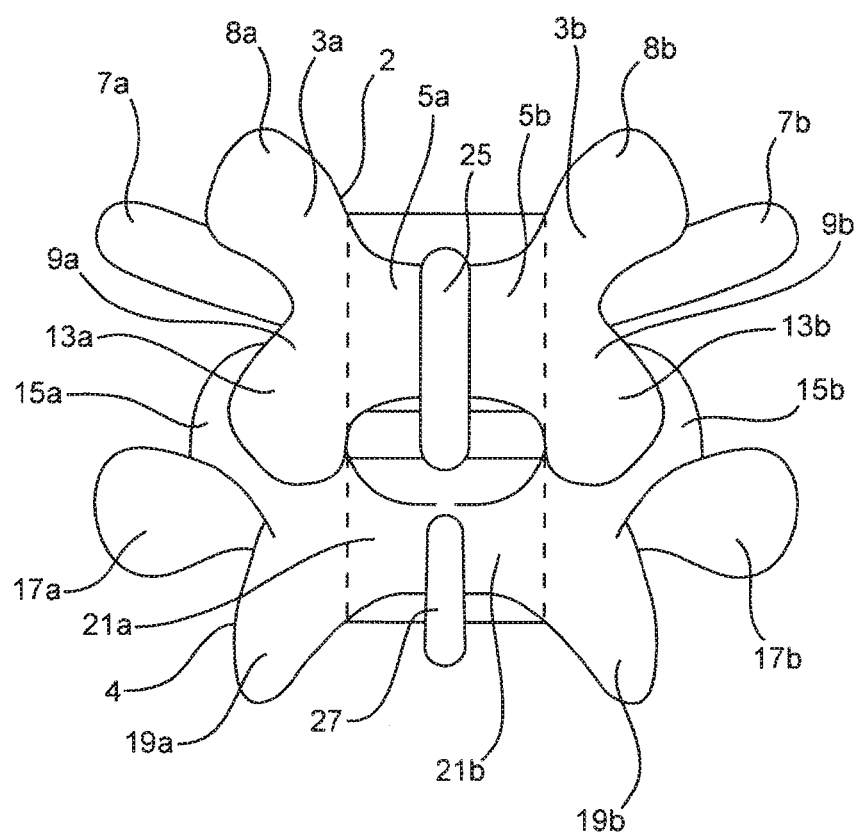
FIG. 1 illustrates a perspective view of a portion of the human spine having two vertebral segments.

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a spinal segment" may include a plurality of such spinal segments and reference to "the screw" includes reference to one or more screw and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention will now be described in greater detail by way of the following description of exemplary embodiments and variations of the devices and methods of the present invention. The invention generally includes an interspinous spacer device as well as instruments for the percutaneous implantation of the interspinous spacer. A key feature of the interspinous spacer device is that it is expandable from a low profile configuration to a higher profile or operative configuration. This design allows the device, when in the low profile condition, to be delivered by percutaneous means without requiring the removal of any portion of the spinal motion segment into which the device is implanted.

Referring now to the drawings and to FIGS. 3A-F in particular, an exemplary interspinous spacer device 10 of the present invention is illustrated in collapsed and expanded configurations, respectively. Interspinous device 10 includes an expandable spacer body 14 that has a size and shape when in the expanded condition for operative positioning between the spinous processes of adjacent superior and inferior vertebrae of the spinal motion segment being treated. It should be noted that embodiments of the current invention may be employed, e.g., as spacers, void creators, etc., and may be particularly useful between the interspinous processes or in other sections of the spine. However, other embodiments may be employed in any other location where a void is desired to be created or filled.

The interspinous device 10 includes a distal end 11 and a proximal end (not shown). At the distal end 11 is disposed a tip 12, which may be made of a biocompatible material such as polymers, metals, nitinol, etc. The expandable member 14 has a distal end 22 and a proximal end 18, with the distal end 22 adjacent the tip 12 and the proximal end 18 adjacent a delivery shaft 16. Interior of the delivery shaft 16 and the expandable member 14, and coupled to tip 12, is a central shaft 24.

The expandable spacer body 14 is generally formed by a helical body having a cross-sectional shape that varies along at least a portion of a longitudinal axis such that longitudinal translation of the proximal end 18 towards the distal end 22, or vice-versa or both, effectively squeezing the expandable spacer body 14 in a longitudinal fashion, causes portions of the expandable spacer body 14 to expand to provide a spacer support between the spinous processes. In particular, various portions of the expandable spacer body 14 expand in a radial dimension from a value $r_0$ to a value $r > r_0$, up to a maximum value of $r_{max}$. In certain embodiments, the axial dimension of the expandable spacer body in the undeployed configuration is greater than that in the deployed configuration.

The distal end 22 of the expandable spacer body may be affixed to the tip 12 and to the central shaft 24 such that a sliding longitudinal translation of the proximal end 18 over the central shaft leads to expansion. Various other combinations of affixations and sliding members may also be employed. In general, the longitudinal translation over a distance x leads to expansion of the expandable spacer body 14.

The expandable spacer body 14 is made of a biocompatible material such as a non-porous material, e.g., nitinol, polymers, or titanium. The shaft 16 may be made of various biocompatible materials, including titanium, stainless steel, etc. The spacer body and/or the shaft may be coated with a lubricious coating or other such treatment to facilitate sliding. These may include, e.g., Teflon®, silicone, surface energy treatments, etc.

As noted above, translation of the proximal and distal ends towards each other leads to radial expansion of portions of the expandable spacer body 14. In more detail, the expandable spacer body 14 is formed of a helical body. The cross-section of the helical body changes to cause the expansion upon longitudinal translation. Referring in particular to FIGS. 3B-3E, cross-sections of various helical segments 14a, 14b, 14c, . . . , 14max, . . . , 14n are shown for a helical body having n turns.

Of course, it is noted that these elements reflect cross-sections that in an actual device may be continuously changing along the helix. For clarity, these two-dimensional cross-sections are discussed here, with the understanding that they refer to a three-dimensional helical structure that may be continuously changing in cross-section. For example, portions of the helical body between segments 14b and 14c emerge above the plane of the page and descend below the plane of the page. These portions may have cross-sectional shapes that are the same as or different than that of segments 14b and 14c. In general, they may be close to the same, and may be shaped in a fashion intermediate to that of 14b and 14c.

In an unexpanded configuration, all segments 14a-14n may have substantially the same radius $r_0$. In an expanded configuration, as shown in FIGS. 3B and 3C, the radius generally varies from $r_0$ to an $r > r_0$ to $r_{max}$ back to $r > r_0$ and finally back to $r_0$. The segment at $r_{max}$ is denoted 14max. The variation of r with respect to the longitudinal translation x depends on the way the cross-sections of 14a-n vary. As may be seen, the cross-sections of 14a-n may vary not haphazardly but in a regular fashion. Certain typical segment cross-sections may be seen in FIG. 3E.

While the general system of variation of cross-sections depends on the sage and geometry of the desired spacer, some general rules may apply in certain embodiments, but it should be especially noted that these do not apply to all systems. First, 14i may be closer or more similar in shape to 14j than the same is to 14a or 14n. Next, if 14a has a distal edge that is at an angle $\theta_{a1}$ and a proximal edge that is at an angle $\theta_{a2}$, then $\theta_{a1}$ and $\theta_{n2}$ may be equal to zero. If $\theta_{b1}$ up to $\theta_{max1}$, i.e., angles distal of segment 14max, are considered to have a positive value of angle, then $\theta_{max2\,up}$ up to $\theta_{n1}$, i.e., angles proximal to segment 14max, may be considered to have a negative value of angle. For the segment with the maximal radial dimension, 14max, its distal edge may have an angle with opposite sign to that of its proximal edge. It is noted again that these are general statements that hold for certain embodiments but do not hold for others.

Figure 3A:
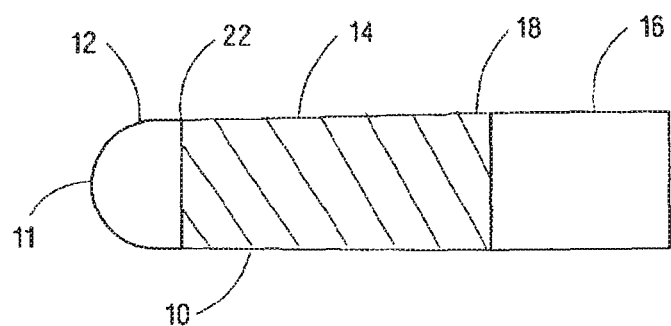
FIG. 3A illustrates a side view of a spacer device according to an embodiment of the present invention in an unexpanded or collapsed state coupled to a cannula of the delivery system of the present invention.
Figure 3B:
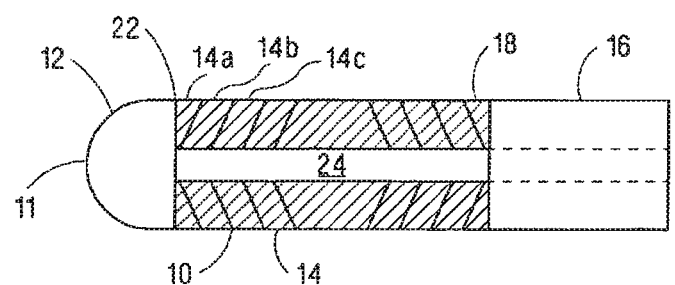
FIG. 3B is a cross-sectional view of a spacer device consistent with FIG. 3A.
Figure 3C:
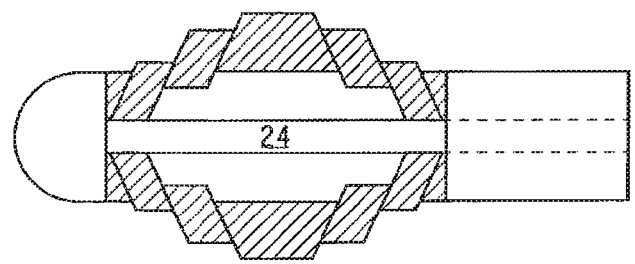
FIG. 3C is a cross-sectional view of the spacer device of FIG. 3A in an expanded configuration.
Figure 3D:
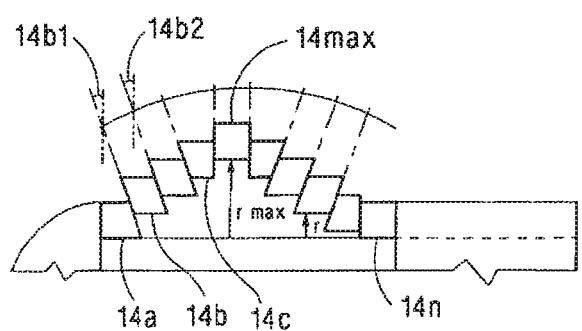
FIG. 3D is a detailed view of the cross-section of an spacer device consistent with FIG. 3A, having oppositely-angled helical turns compared to the embodiment of FIG. 3C, also shown in an expanded configuration, showing the varying cross-section of the continuous helical segment.
Figure 3E:
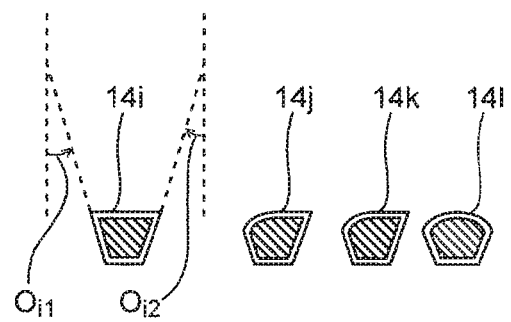
FIG. 3E is a more detailed view of certain of the varying cross-sections of the helical segment.

It is additionally noted that the embodiment of FIGS. 3B and 3C differs from that of FIG. 3D, in that the angles of the segments are the opposite. While the embodiment of FIG. 3D may be easier to implement, either system may be employed.

Figure 3F:
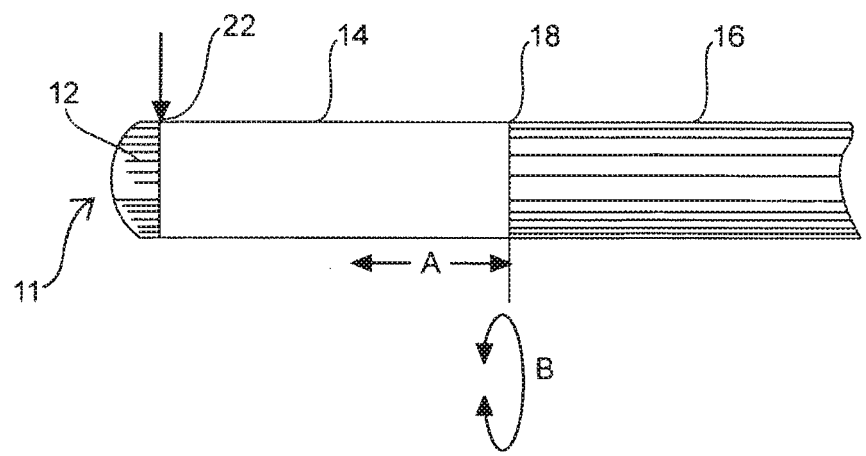
FIG. 3F is a side view illustrating the longitudinal and rotational movements employed in deploying certain embodiments of the invention.

Referring to FIG. 3F, the way in which the longitudinal translation A may occur can vary. In one embodiment, the device may be inserted between the spinous processes in a manner disclosed in, e.g., U.S. patent application Ser. No. 11/190,496, filed Jul. 26, 2005, entitled "SYSTEMS AND METHODS FOR POSTERIOR DYNAMIC STABILIZATION OF THE SPINE", which is incorporated by reference herein in its entirety. One or both of the central shaft 24 or the delivery shaft 16 may be rotated as shown by B to cause the relative motion of the distal end and the proximal end towards each other via a screw, ratchet, or thread arrangement. In general, any deployment arrangement may be employed that causes the relative movement of the distal and proximal ends towards each other. Further details of deployment, arrangements that may be used with embodiments of the current invention are described in the patent application just incorporated by reference above.

Figure 4:
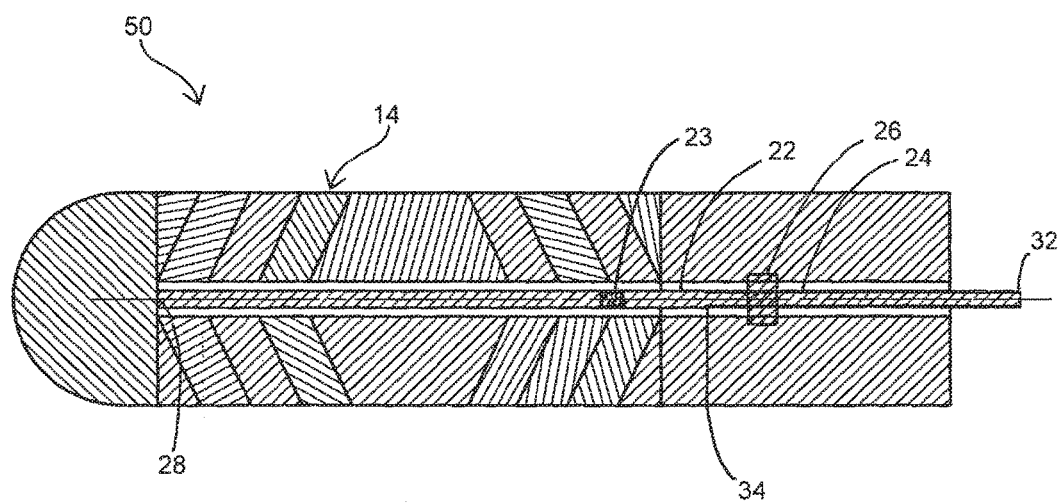
FIG. 4 is a cross-sectional view of a spacer device according to an embodiment of the present invention employing a threaded screw to deploy the device.

As one example, referring to FIG. 4, a method and device for causing translation of the proximal and/or distal ends of the spacer body 50 is shown as employing a threaded shaft assembly 34 having a distal end 28 which is fixed to the distal tip of the device, a proximal end 32, a threaded section 24, and a non-threaded section 22. The threaded shaft assembly may be part of the implanted device or may be removable. In the case of a removable threaded shaft assembly, the assembly 34 is in two parts or is otherwise detachable, e.g., at release element 23. Release element 23 may employ a magnet to releasably hold the two segments together, a fusible link, a "pull-out" or threaded shaft, and so on.

A fixed segment or threaded module 26 is provided which the threaded segment may be rotated against to, e.g., pull the distal tip toward the proximal end to deploy the spacer. In an alternative embodiment, a balloon or other such expandable member within the device may be employed to expand the same in the absence of a compressional force. A "filler" material can be disposed within the helical spacer body to maintain the expansion. This may include compressible materials such as elastomers or uncompressible materials such as cements. A locking mechanism may be similarly employed, and the locking may be permanent or reversible. In a related embodiment, the locking may allow a limited range of translation, including translation after the device is implanted, to accommodate movement, loads, etc.

The device may be afforded a capability to reposition the same following implantation, and this reposition may be done in a minimally-invasive manner. For example, a tool may be percutaneously placed to engage the compression assembly, e.g., to turn the screw, or to provide additional compression or tension which corresponds to additional radial expansion or contraction.

Figure 5:
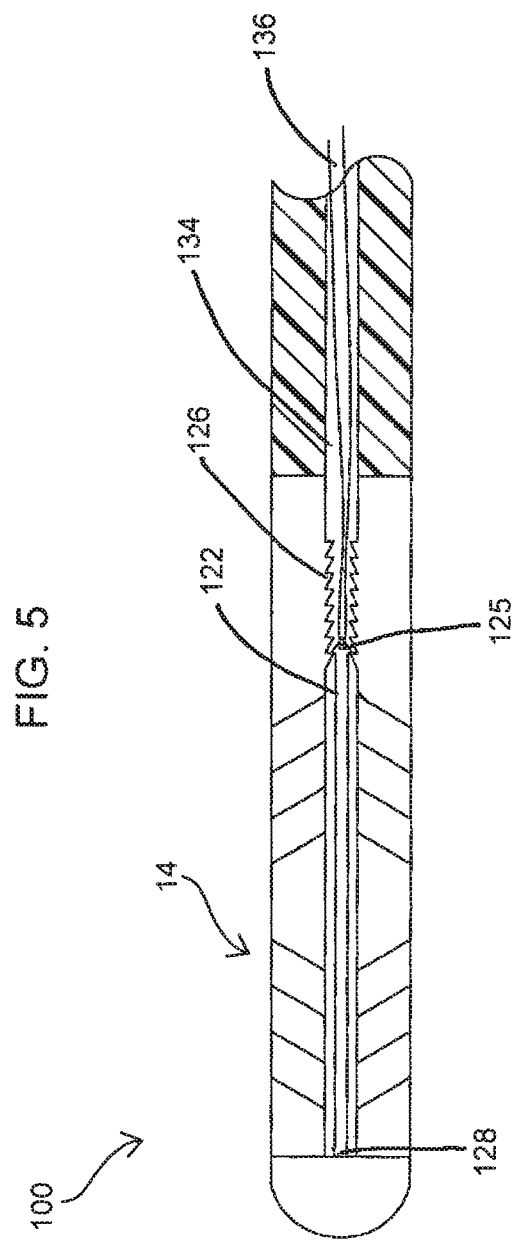
FIG. 5 is a cross-sectional view of a spacer device according to an embodiment of the present invention employing a ratchet to deploy the device.

In an alternative embodiment, as shown in FIG. 5, a ratchet assembly 100 is shown with an expandable body 14, a distal ratchet shaft 122 with a proximal catch 125, a one-way ratchet 126, a proximal ratchet lumen 134, and a deployment pull string 136. In use, by pulling pull string 136, catch 126 moves in a one-way manner into ratchet 126, compressing body 14 and expanding the spacer body 14. A release mechanism as described can be employed to detach the spacer body from the deployment device.

Figure 6:
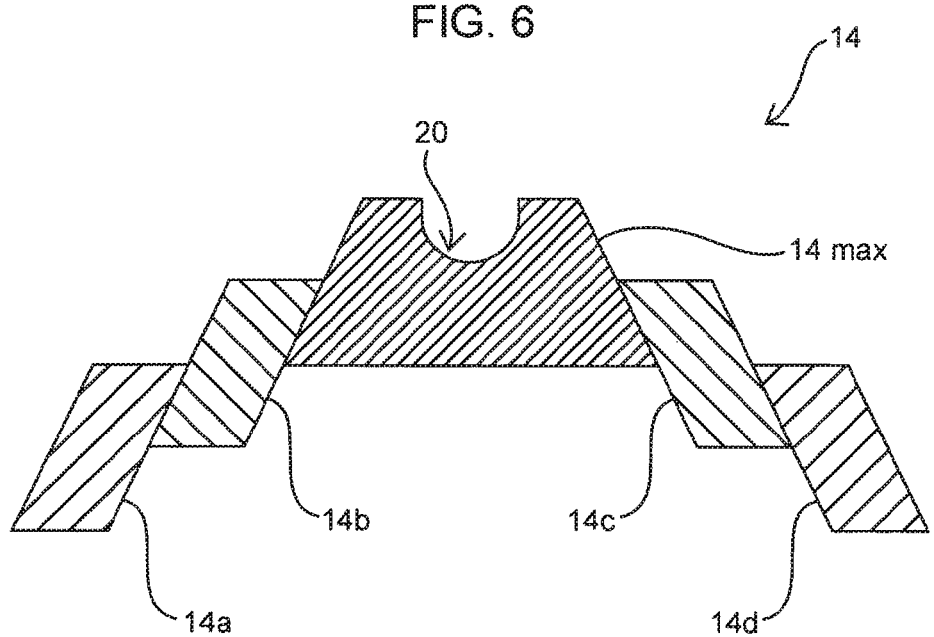
FIG. 6 is a cross-sectional view of a spacer device according to an embodiment of the present invention employing a groove to engage a segment of the vertebrae.

Referring to FIG. 6, for any of the embodiments, the spacer body 14 may include a void or recess 20 which may be employed to capture or engage a vertebral segment such as an interspinous process.

Figure 7:
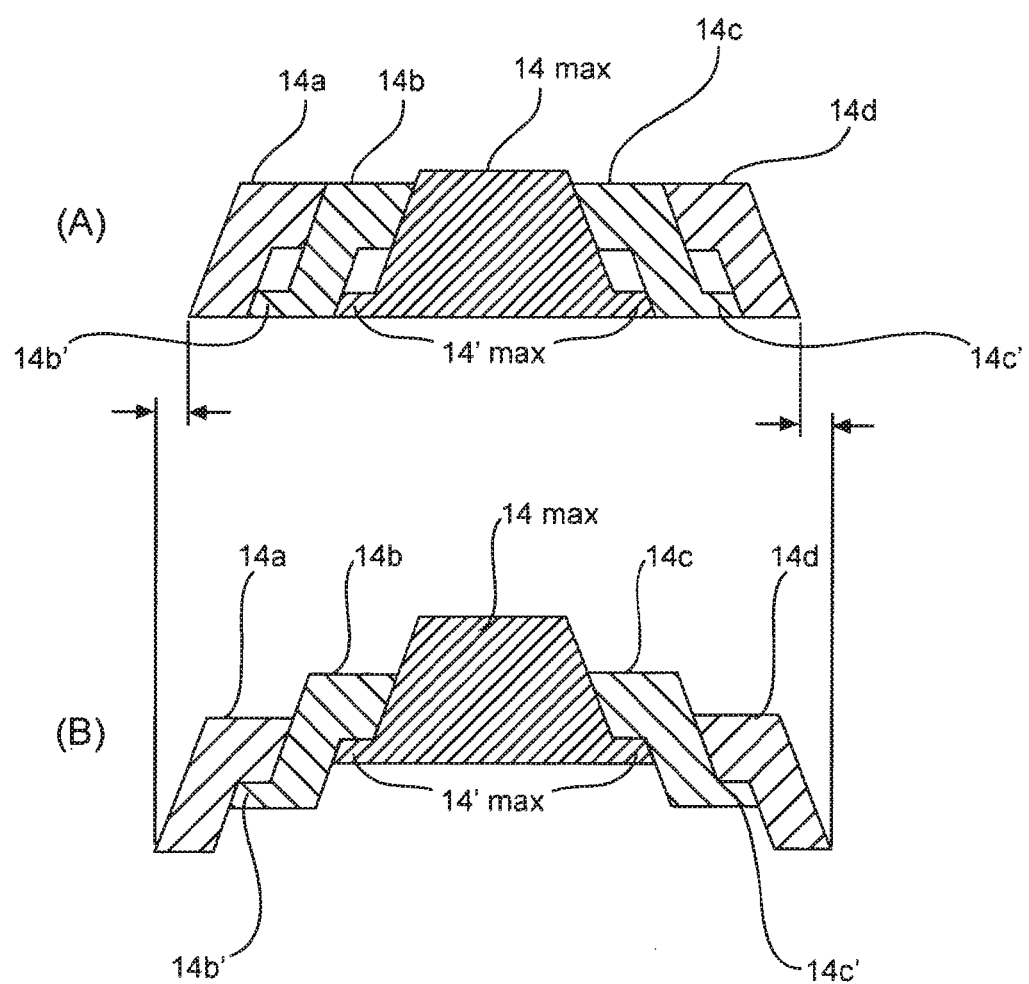
FIGS. 7(A) and (B) illustrate stages of deployment of a spacer device according to an embodiment of the present invention employing cooperating segments.

Referring to FIG. 7, the spacer segments 14i may be provided with tracks, tongues, or grooves, etc., between the translating elements to facilitate sliding, limit travel, prevent undesired rotation, torquing, stabilize the elements, force directionality of motion, etc. In FIG. 7, the same are shown as projections 14i' on each side of segment 14i. Segment 14i is intended to generally refer to a generic segment. In FIG. 7, only segments 14a-14d and 14max are shown. FIG. 7(A) shows an undeployed configuration, and FIG. 7(B) shows a deployed configuration.

Figure 8:
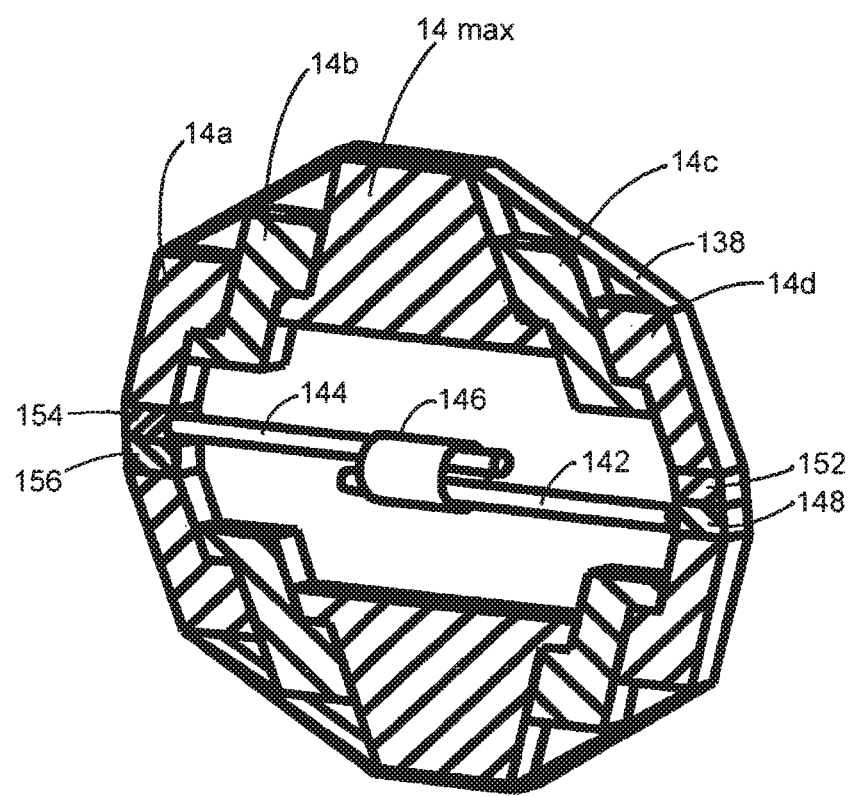
FIG. 8 shows a spacer device according to an embodiment of the present invention employing a drive module.

FIG. 8 shows a perspective cross-sectional segment of an alternative embodiment of a spacer body according to the principles of the invention. Similar elements have similar reference numerals as the figures above, and are not described again. The embodiment of FIG. 8 further includes a covering 138 and a drive module 146. The covering 138 may be, e.g., a mesh bag, a balloon, etc. The drive module 146 is shown coupled to rods 142 and 144, and allow deployment of the device in an automatic fashion. The drive module may include a power supply such as an integral battery, may be controlled wirelessly, and may have one or two (as shown) motorized lead screws. One rod 144 may be coupled to distal end 154, and the other rod 142 may be coupled to proximal end 148. Alternatively, proximal end 152 and distal end 156 may be employed.

Figure 9:
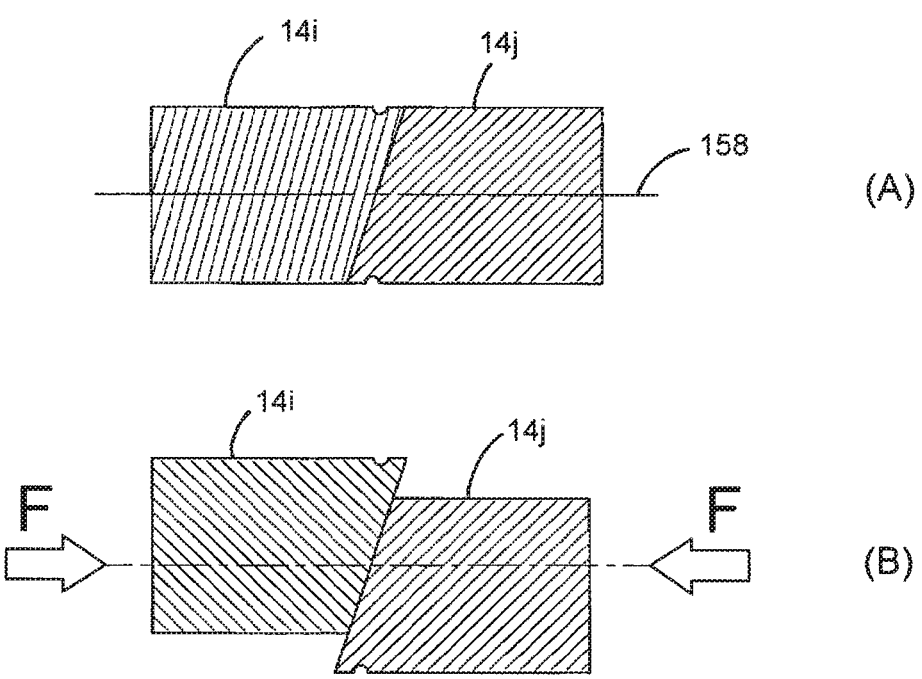
FIG. 9 shows a portion of a spacer device employing a generic set of elements that move radially upon application of a force along an axis.

It should be noted that while a helical body is shown, the same is not required in certain embodiments of the invention. For example, as shown in FIG. 9, any system with two or more elements 14i, 14j, may be employed, where compression causes one element or both to move radially away from a central axis 158. In this system, the first element has a first surface that mates with a second surface of a second element, and the mating surfaces lie at an angle not equal to 90 degrees from the central axis 158. The compressive force exerted between the first and second elements, acting along axis 158, causes either or both to move radially away from the central axis.

In certain embodiments, the expandable body is made of a non-compliant or semi-compliant material so as to maintain a substantially fixed shape or configuration and ensure proper, long-term retention within the implant site. In other embodiments, the expandable member may be made of a compliant material. In any embodiment, the compressibility and flexibility of can be selected to address the indications being treated.

In certain embodiments of present invention, either during the implant procedure or in a subsequent procedure, the size or volume of the implanted expandable spacer may be selectively adjusted or varied. For example, after an initial assessment upon implant, it may be necessary to adjust, either reduce or increase, the size or volume of the spacer to optimize the intended treatment. Further, it may be intended to only temporarily implant the spacer for the purpose of treating a temporary condition, e.g., an injured or bulging or herniated disk. Once the repair is achieved or the treatment completed, the spacer may be removed, either with or without substantially reducing the size or volume of the spacer. In other embodiments, the spacer may be made of biodegradable materials wherein the spacer degrades after a time in which the injury is healed or the treatment completed.

When unexpanded or deflated, as shown in FIGS. 3A and 3B, the expandable spacer body 14 has a low profile, such as a narrow, cylindrical, elongated shape, to be easily translated through a delivery cannula.

The device may further include radiopaque markers on the surface of the expandable body 14 visible under fluoroscopic imaging to facilitate positioning of the expandable body. Any number of markers may be employed anywhere on the expandable body 14, or the helical body itself may be radiopaque. Other markers may also be employed, including ultrasound markers. Any of the markers described, or other such markers, may be employed to determine the level of deployment or the sufficiency of deployment. For example, two markers may be disposed on the device such that if the markers are seen to be in a particular alignment, the device is considered to be fully deployed. One of ordinary skill in the art given this teaching will see numerous other ways in which the use of markers can provide significant information about the position, orientation, and deployment of the device.

Once installed, the interspinous device may be further secured to the spinous processes 18, 22 to ensure that the expandable body does not slip or migrate from its implanted position. Any type of anchoring means, such as screws, tacks, staples, adhesive, etc. may be employed. The delivery shaft 16 may be removed from the expandable spacer body 14 using devices and techniques disclosed in the patent application incorporated by reference above.

The subject devices and systems may be provided in the form of a kit which includes at least one interspinous device of the present invention. A plurality of such devices may be provided where the devices have the same or varying sizes and shapes and are made of the same or varying biocompatible materials. Possible biocompatible materials include polymers, plastics, ceramic, metals, e.g., titanium, stainless steel, tantalum, chrome cobalt alloys, etc. The kits may further include instruments and tools for implanting the subject devices, including but not limited to, a cannula, a trocar, a scope, a device delivery/inflation/expansion lumen, a cutting instrument, a screw driver, etc., as well as a selection of screws or other devices for anchoring the spacer to the spinous processes. Instructions for implanting the interspinous spacers and using the above-described instrumentation may also be provided with the kits.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof; are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A device for stabilizing at least one spinal motion segment comprising a first vertebra having a first spinous process and a second vertebra having a second spinous process, the device comprising:
    a helical body including a first spinous process-receiving recess, a second spinous process-receiving recess, and at least two segments, the at least two segments physically contact each other such that a force provided by a delivery device detachably coupled to the device causes one or both of the segments to move in a direction with a component substantially perpendicular to a longitudinal axis of the device, the helical body having a cross-sectional shape that varies along at least a portion of the longitudinal axis, the helical body having an undeployed configuration with an axial dimension and a radial dimension substantially transverse to the axial dimension, and a deployed configuration having an axial dimension and a radial dimension substantially transverse to the axial dimension such that the first and second spinous process-receiving recesses move away from one another when the helical body moves from the undeployed configuration to the deployed configuration, and wherein the radial dimension of at least a portion of the helical body in the undeployed configuration is less than the radial dimension of at least a portion of the helical body in the deployed configuration.

2. The device of claim 1, wherein the axial dimension of the undeployed configuration is greater than the axial dimension in the deployed configuration.

3. The device of claim 1, wherein a distal end of the helical body is coupled to a tip.

4. The device of claim 1, wherein the device in the undeployed configuration has a cylindrical shape.

5. The device of claim 1, wherein the cross-sectional shape of the helical body varies smoothly.

6. The device of claim 1, wherein the cross-sectional shape of the helical body varies continuously.

7. The device of claim 1, further comprising a threaded shaft assembly coupled to the helical body, such that rotation of the threaded shaft assembly causes the deployment or undeployment of the helical body.

8. The device of claim 1, further comprising a ratchet assembly and catch coupled to the helical body, such that movement of the catch relative to the ratchet assembly causes the deployment of the helical body.

9. The device of claim 7, further comprising a release mechanism within the threaded shaft assembly, to allow removal of a portion of the threaded shaft assembly following deployment.

10. The device of claim 8, further comprising a release mechanism within the ratchet assembly, to allow removal of a portion of the ratchet assembly following deployment.

11. The device of claim 1, wherein the helical body includes a plurality of helical segments, and wherein at least one helical segment has a projection for engaging an adjacent helical segment.

12. The device of claim 1, wherein the helical body includes a covering.

13. The device of claim 1, wherein the delivery device comprises a drive module coupled to the helical body, such that operation of the drive module causes the deployment of the helical body.

14. A system for stabilizing at least one spinal motion segment comprising a first vertebra having a first spinous process and a second vertebra having a second spinous process and an interspinous space defined between the first and second spinous processes, the system comprising:
    the device of claim 1; and
    a delivery device for delivering the device in the undeployed configuration within the interspinous processes and for radially expanding the device from the undeployed configuration to the deployed configuration.

15. The system of claim 14, wherein the device is configured for delivery by the delivery device through a midline incision.

16. A method for stabilizing a vertebra relative to another vertebra wherein the vertebrae define an interspinous space therebetween, the method comprising:
    introducing the device of claim 1 within the interspinous space when in the undeployed configuration; and
    radially expanding the device to selectively distract the spinous processes.

17. The method of claim 16, further comprising forming an incision along the midline above the interspinous space, wherein the introducing the interspinous device comprises inserting the device within the midline incision.

18. A device for stabilizing at least one spinal motion segment comprising a first vertebra having a first spinous process and a second vertebra having a second spinous process, the device comprising:
    a helical body having a cross-sectional shape that varies along at least a portion of a longitudinal axis, wherein the helical body has an undeployed configuration with an axial dimension and a radial dimension substantially transverse to the axial dimension, and a deployed configuration having an axial dimension and a radial dimension substantially transverse to the axial dimension, wherein the radial dimension of at least a portion of the helical body in the undeployed configuration is less than the radial dimension of at least a portion of the helical body in the deployed configuration;

a tip disposed adjacent to and distal to a distal end of the helical body; and a shaft disposed adjacent to and proximal of a proximal end of the helical body, wherein each turn of the helical body has a distal edge and a proximal edge, and wherein the angle formed between the distal edge of a distal turn of the helical body and the tip is substantially zero, and wherein the angle formed between the proximal edge of a proximal turn of the helical body and the shaft is substantially zero.

19. The device of claim 18, wherein in the deployed configuration a turn of the helical body has a maximal radial dimension, and wherein the angle of each distal and proximal edge, on each side of the turn with the maximal radial dimension, excepting the proximal-edge of the proximal turn and the distal edge of the distal turn, has the same sign.

20. The device of claim 19, wherein the proximal edge and the distal edge of the turn with the maximal radial dimension in the deployed configuration have opposite signs.

21. An implantable interspinous device for delivery to an interspinous space by a lateral approach, the implantable interspinous device comprising:

a first tapered section having an axial dimension and a radial dimension that is substantially transverse to the axial dimension, the radial dimension varies along at least a portion of a longitudinal axis of the implantable interspinous device, wherein at least a portion of the first tapered section has a helical configuration;

a second tapered section;

at least one spinous process-receiving recess positioned between the first tapered section and the second tapered section such that the first and second tapered sections extend away from opposite sides of the interspinous space when first and second spinous processes of a subject are positioned in the at least one spinous process-receiving recess.

22. The implantable interspinous device of claim 21, wherein the at least one spinous process-receiving recess includes a first spinous process-receiving recess and a second spinous process-receiving recess configured to hold the first and second spinous processes, respectively.

23. The implantable interspinous device of claim 21, further comprising one or more central segments that define the at least one spinous process-receiving recess, the one or more central segments extending between the first and second tapered sections.

24. The implantable interspinous device of claim 21, wherein the implantable interspinous device has a generally circular cross-sectional shape.

* * * * *

UNITED STATES PATENT AND TRADEMARK OFFICE
CERTIFICATE OF CORRECTION

PATENT NO. : 10,058,358 B2  
APPLICATION NO. : 15/268844  
DATED : August 28, 2018  
INVENTOR(S) : Altarac et al.

Page 1 of 1

It is certified that error appears in the above-identified patent and that said Letters Patent is hereby corrected as shown below:

In the Drawings

Figure 2A:
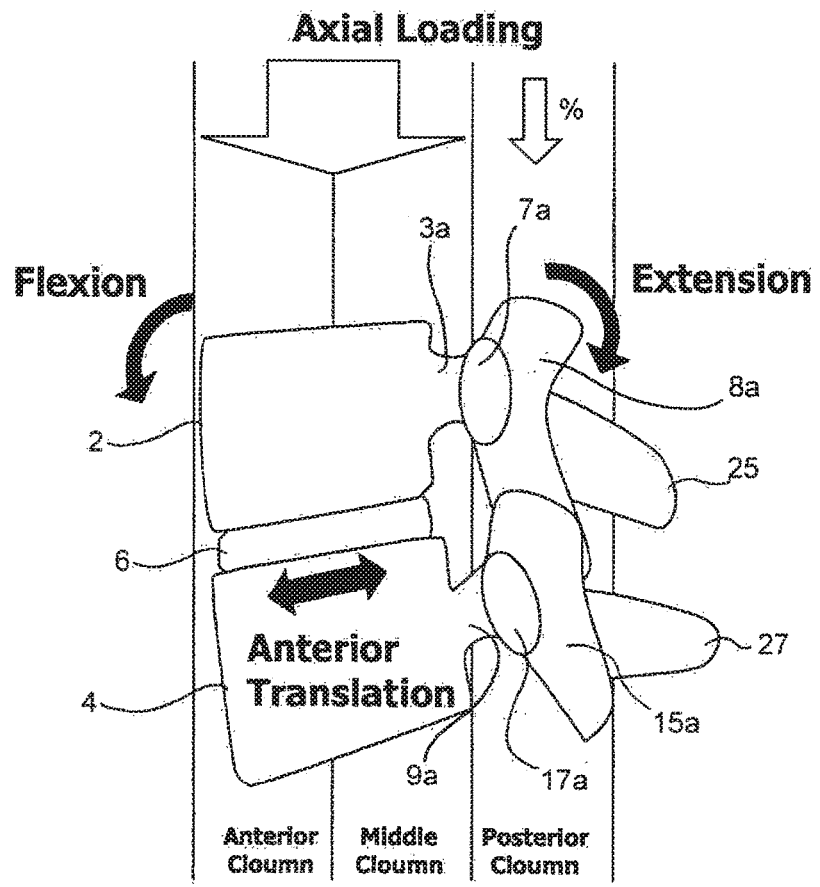
FIGS. 2A, 2B and 2C illustrate left side, dorsal and top views, respectively, of the spinal segments of FIG. 1A under going various motions.
Figure 2B:
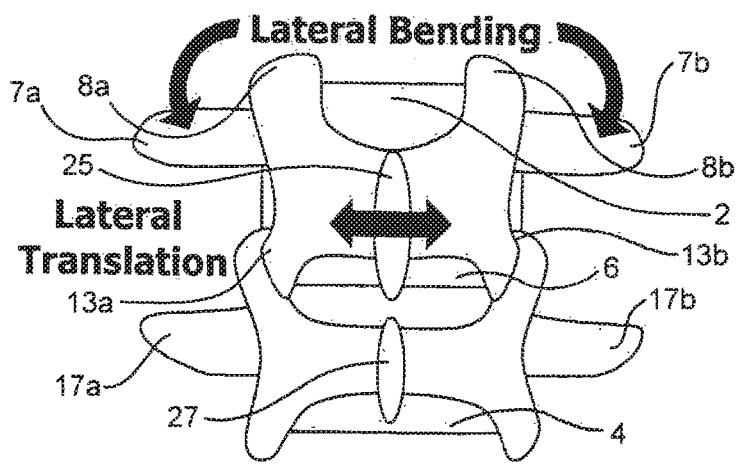
Figure 2C:
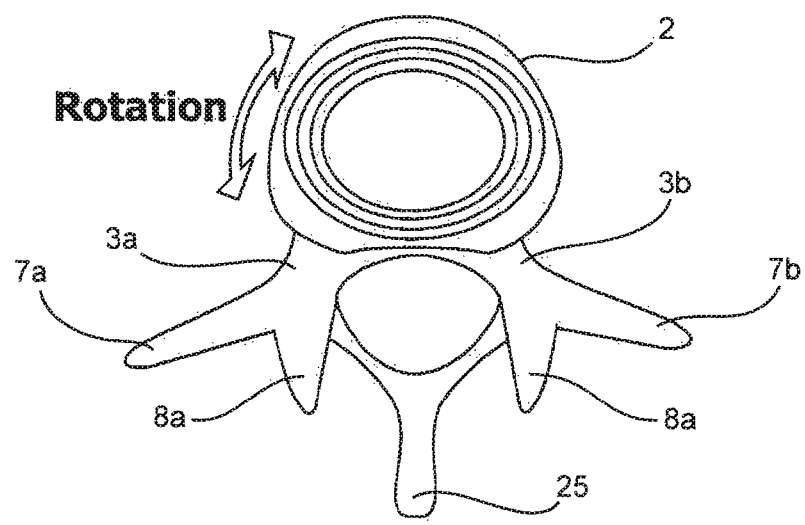

On sheet 2 of 14, in FIG. 2A, delete "Anterior Cloumn" and insert -- Anterior Column --, therefor.

On sheet 2 of 14, in FIG. 2A, delete "Middle Cloumn" and insert -- Middle Column --, therefor.

On sheet 2 of 14, in FIG. 2A, delete "Posterior Cloumn" and insert -- Posterior Column --, therefor.

In the Specification

In Column 2, Line 40, delete "spondylolithesis," and insert -- spondylolisthesis, --, therefor.

In Column 2, Line 40-41, delete "spondylotlisthesis," and insert -- spondylolisthesis, --, therefor.

In Column 3, Line 52, delete "Nos." and insert -- No. --, therefor.

In Column 5, Line 12, delete "ipsolateral" and insert -- ipsilateral --, therefor.

In Column 8, Line 21, delete "sage" and insert -- usage --, therefor.

In Column 8, Line 29, delete "$\Theta_{max2\ up}$" and insert -- $\Theta_{max2}$ --, therefor.

In Column 11, Line 21, delete "thereof;" and insert -- thereof, --, therefor.

Signed and Sealed this  
Twenty-second Day of January, 2019

Andrei Iancu  
*Director of the United States Patent and Trademark Office*